United States Patent [19]

Sprecker et al.

[11] 4,263,149

[45] Apr. 21, 1981

[54] 2-OXABICYCLOOCTANE DERIVATIVES FOR AUGMENTING OR ENHANCING THE FLAVOR OF FOODSTUFFS

[75] Inventors: Mark A. Sprecker, Sea Bright; Frederick L. Schmitt, Holmdel; Manfred H. Vock, Locust; Joaquin F. Vinals, Red Bank, all of N.J.; Jacob Kiwala, Brooklyn, N.Y.

[73] Assignee: International Flavors & Fragrances Inc., New York, N.Y.

[21] Appl. No.: 46,361

[22] Filed: Jun. 7, 1979

Related U.S. Application Data

[62] Division of Ser. No. 953,128, Oct. 20, 1978, Pat. No. 4,195,099.

[51] Int. Cl.$^3$ .................... D06M 13/18; D06M 13/16
[52] U.S. Cl. .................................. 252/8.9; 260/345.1; 252/8.6
[58] Field of Search ....................... 252/8.9; 200/345.1

[56] References Cited

PUBLICATIONS

Chem. Abs., vol. 88 (1978) 177030/c "Use of Bicyclic Oxygen Containing Compound as Perfume and/or Aroma Ingredient".

*Primary Examiner*—Joseph L. Schofer
*Assistant Examiner*—Herbert J. Lilling
*Attorney, Agent, or Firm*—Arthur L. Liberman

[57] ABSTRACT

Described are derivatives of 2-oxabicyclo[2.2.2]octanes and precursors therefor, cyclohexenemethanols as well as lower alkyl esters of said cyclohexenemethanols. The oxabicyclooctanes are useful in perfumery and foodstuff, medicinal product and tobacco flavors. The cyclohexenemethanols are useful as precursors for the oxabicyclooctanes and are, themselves, useful for their organoleptic properties in perfumery and flavors as are the esters of said cyclohexenemethanols.

10 Claims, 44 Drawing Figures

GLC PROFILE FOR EXAMPLE IB

GLC PROFILE FOR EXAMPLE IA

NMR SPECTRUM FOR EXAMPLE IA

IR SPECTRUM FOR EXAMPLE IA

NMR SPECTRUM FOR EXAMPLE IB

IR SPECTRUM FOR EXAMPLE IB.

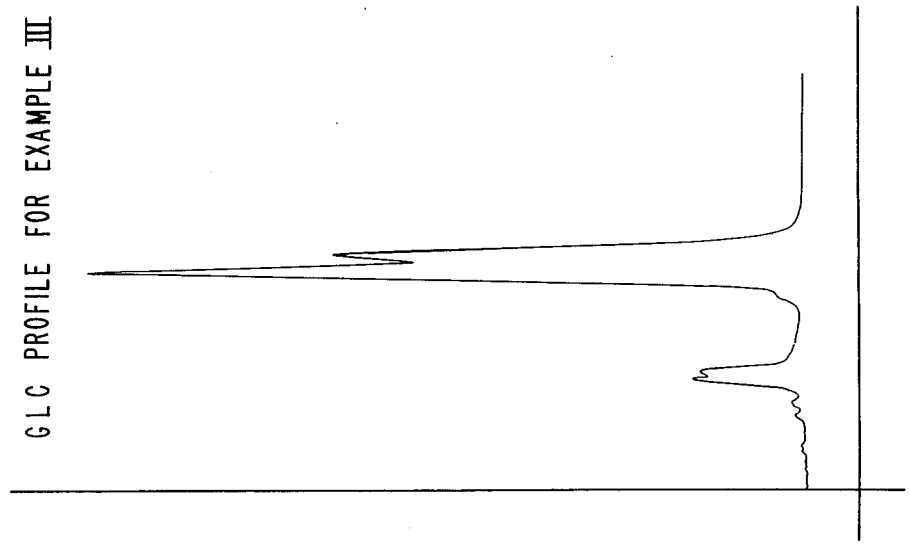
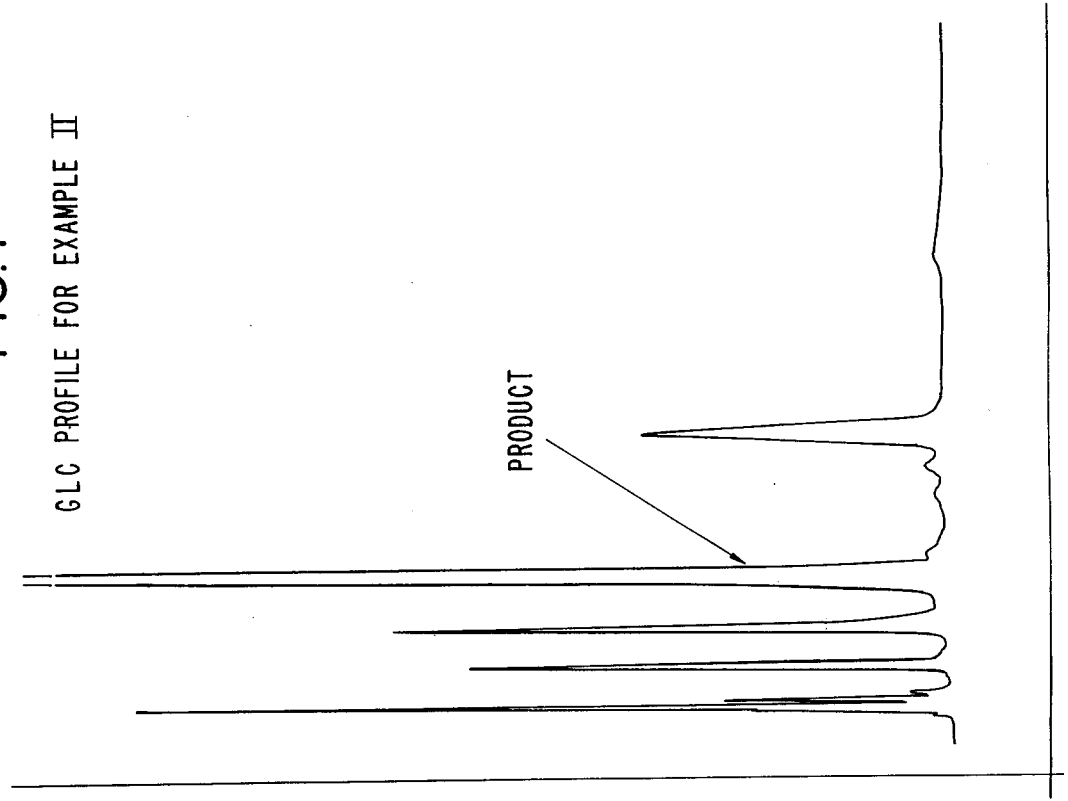

NMR SPECTRUM FOR EXAMPLE II.

IR SPECTRUM FOR EXAMPLE II

NMR SPECTRUM FOR EXAMPLE III.

IR SPECTRUM FOR EXAMPLE III.

NMR SPECTRUM FOR EXAMPLE IV.

IR SPECTRUM FOR EXAMPLE IV.

NMR SPECTRUM FOR EXAMPLE V (A).

IR SPECTRUM FOR EXAMPLE V (A).

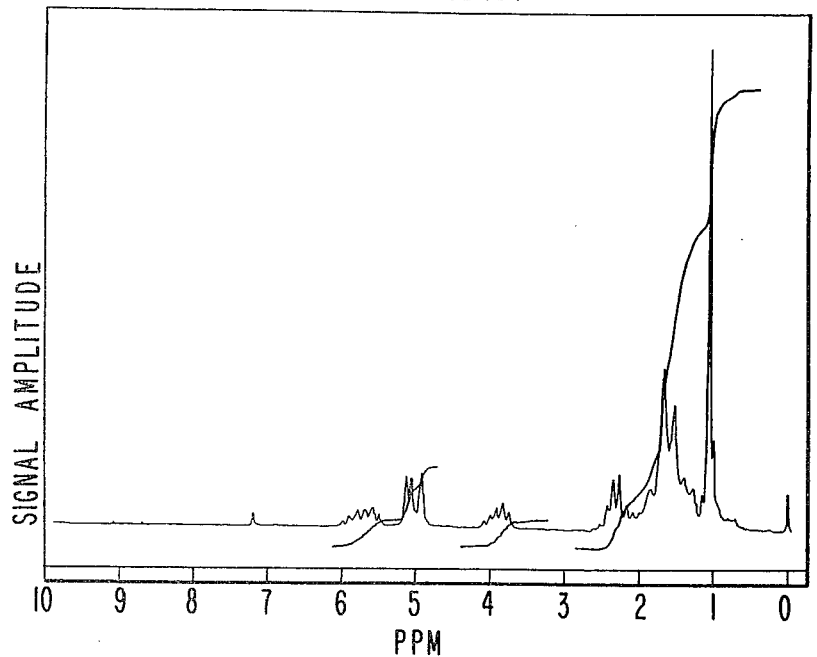
FIG.17
FIG.18
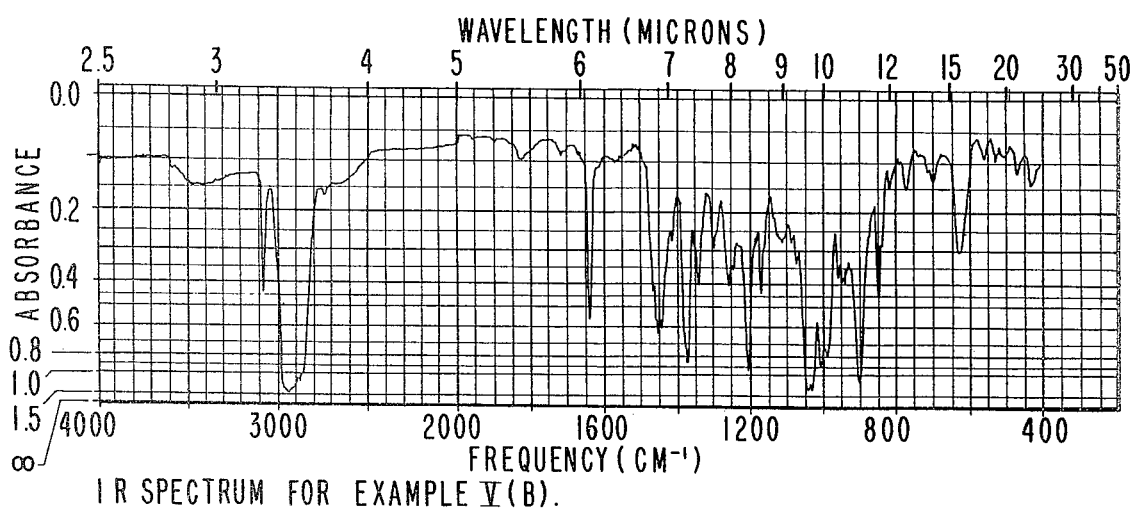

GLC PROFILE FOR EXAMPLE VI (B)

GLC PROFILE FOR EXAMPLE VI (A)

IR SPECTRUM FOR EXAMPLE VI (B).

GLC PROFILE FOR EXAMPLE VII (A)

NMR SPECTRUM FOR EXAMPLE VII(A).

IR SPECTRUM FOR EXAMPLE VII(A).

FIG. 25
GLC PROFILE FOR EXAMPLE VII(B).
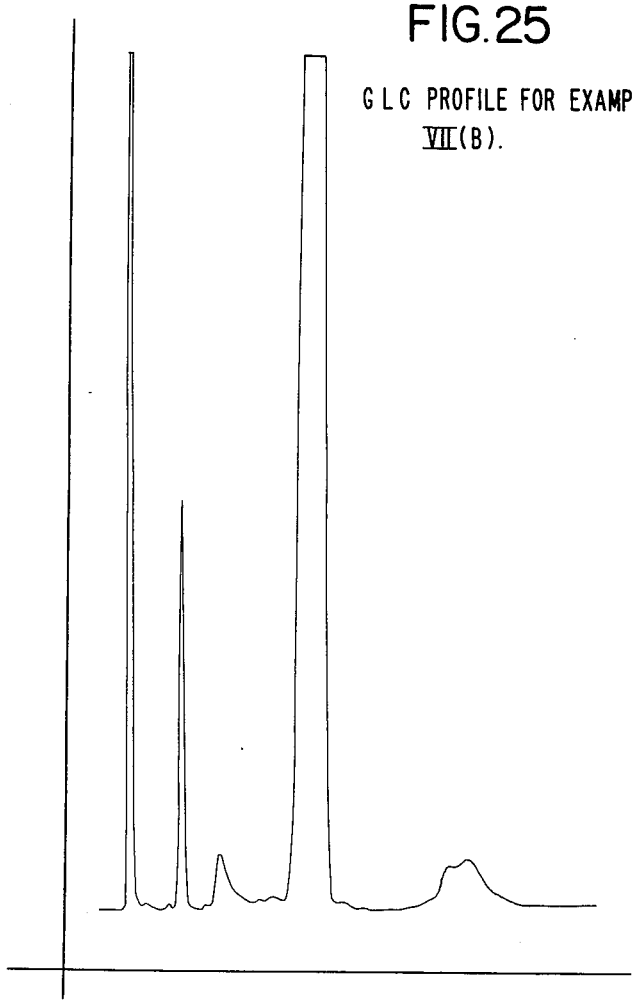
NMR SPECTRUM FOR EXAMPLE VII(B).
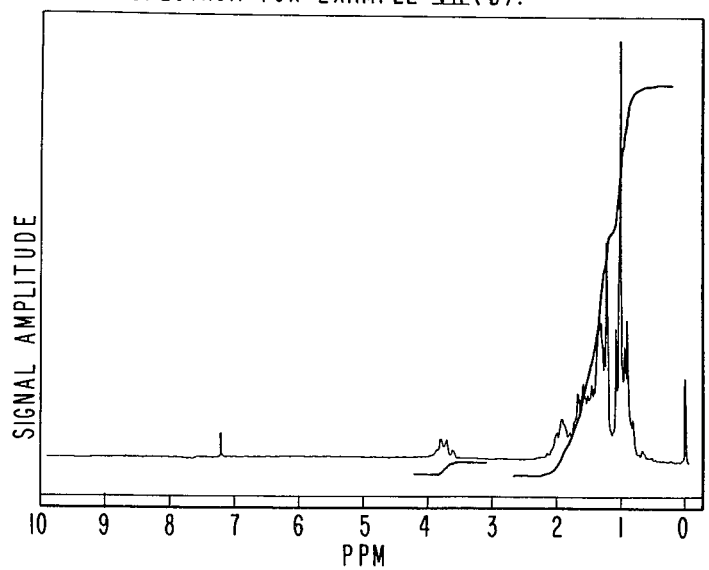
FIG. 26

IR SPECTRUM FOR EXAMPLE VII(B).

GLC PROFILE FOR EXAMPLE VIII

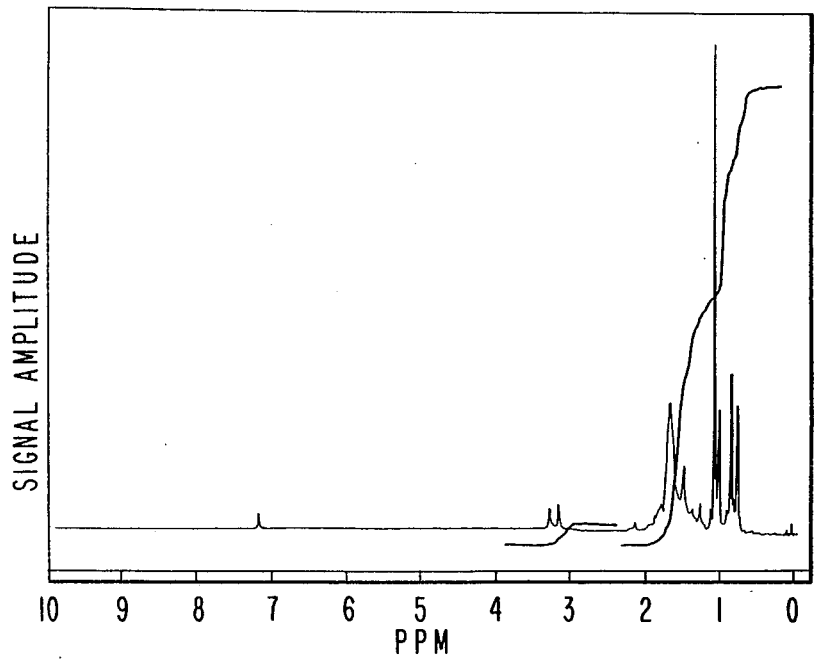
FIG. 29
NMR SPECTRUM FOR EXAMPLE VIII
FIG. 30
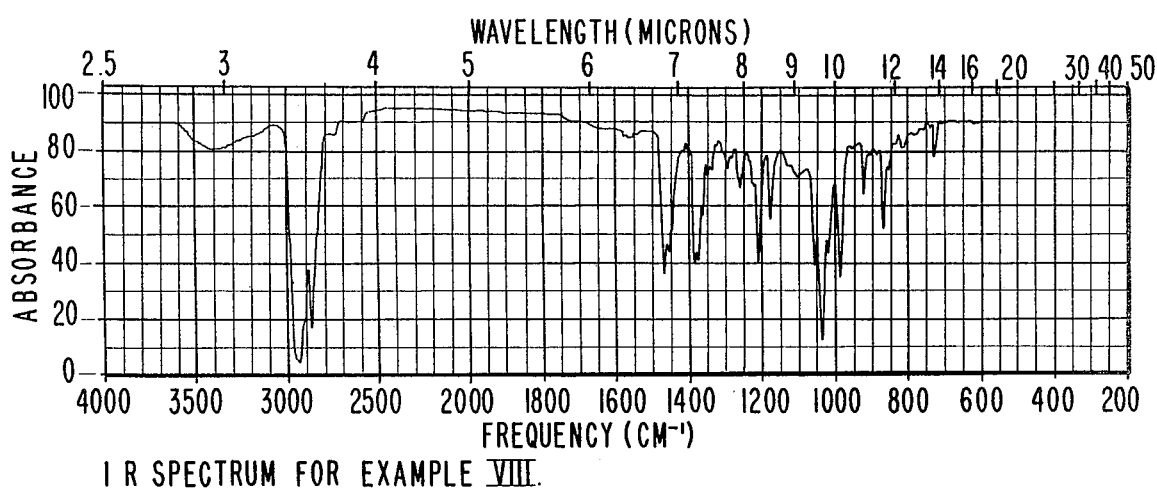
IR SPECTRUM FOR EXAMPLE VIII.

FIG.31
GLC PROFILE FOR EXAMPLE IX
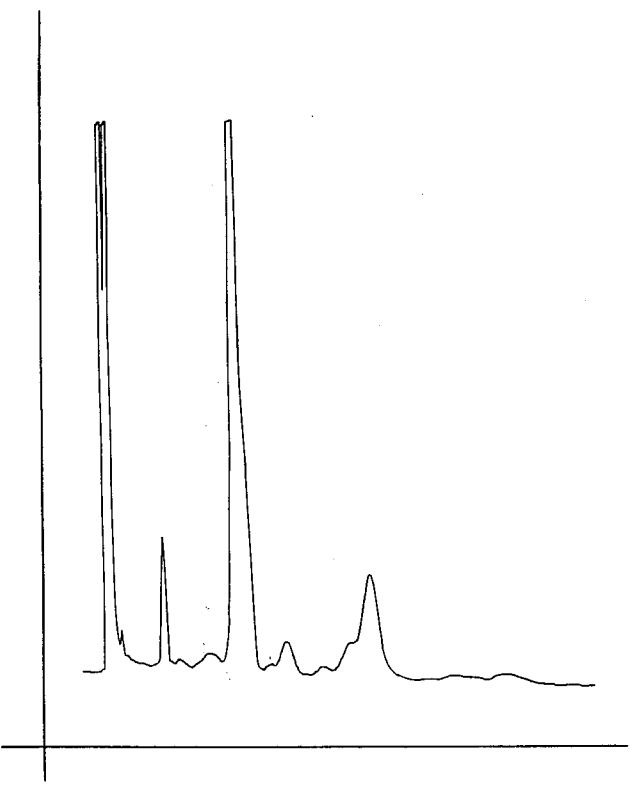
NMR SPECTRUM FOR EXAMPLE IX.
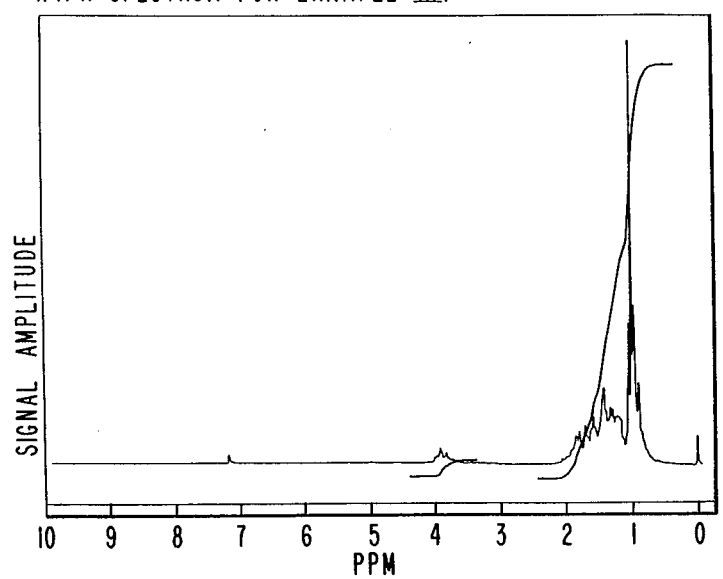
FIG.32

IR SPECTRUM FOR EXAMPLE IX.

GLC PROFILE FOR EXAMPLE X

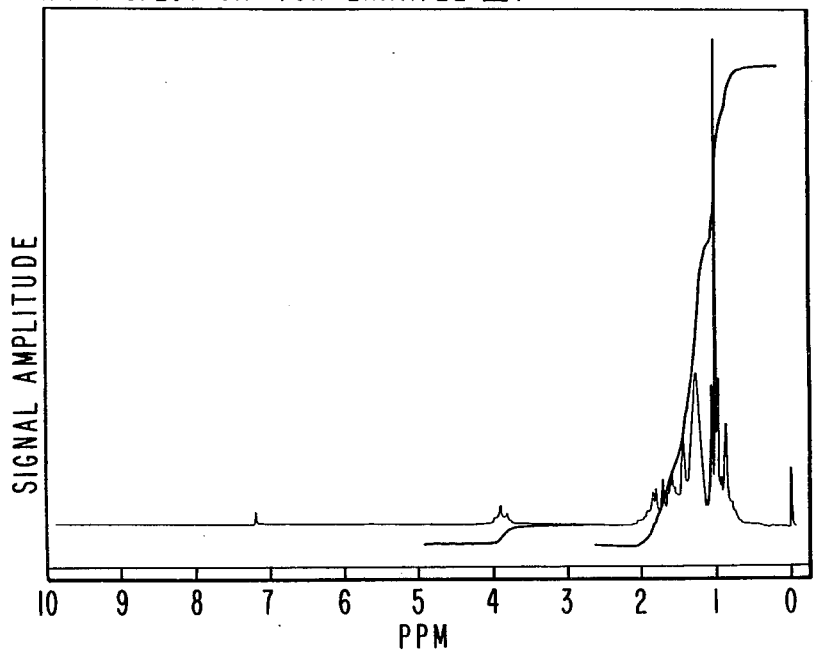
FIG.35
FIG.36
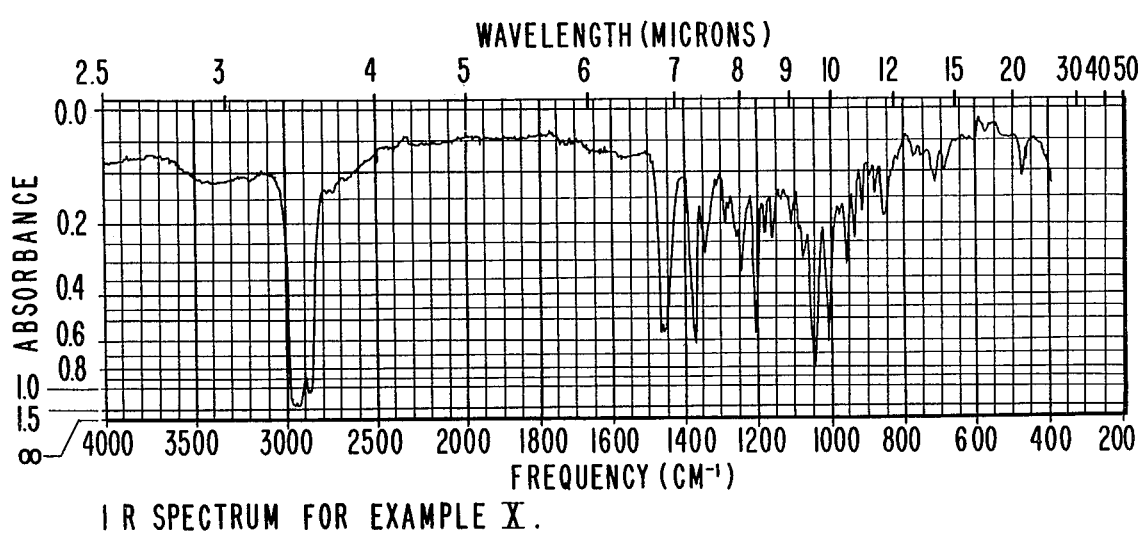

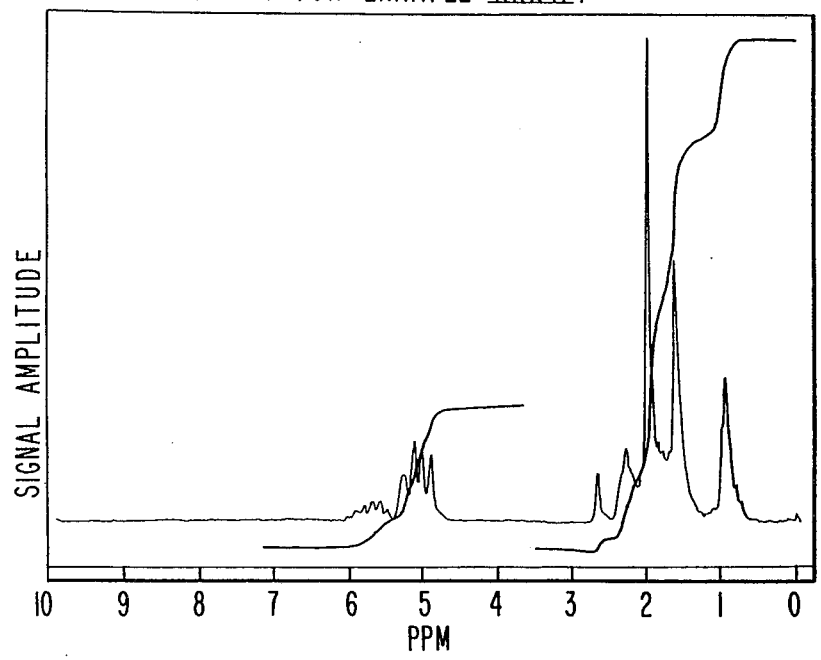
FIG. 37
FIG. 38
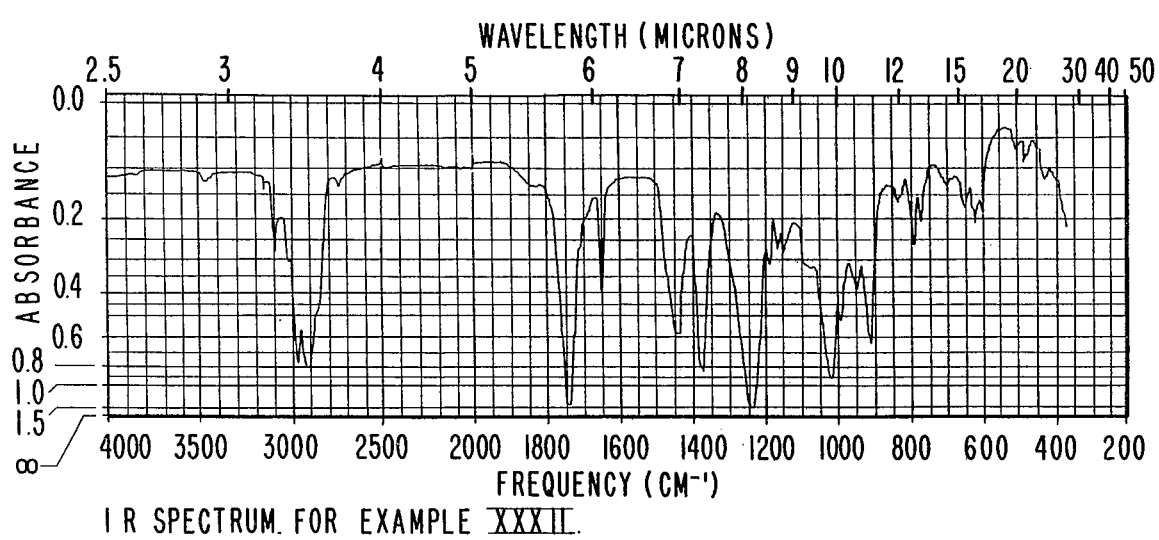

GLC PROFILE FOR EXAMPLE XXXIII

NMN SPECTRUM FOR EXAMPLE XXXIII

IR SPECTRUM FOR EXAMPLE XXXIII

GLC PROFILE FOR EXAMPLE XXXIV

NMR SPECTRUM FOR EXAMPLE XXXIV.

IR SPECTRUM FOR EXAMPLE XXXIV.

2-OXABICYCLOOCTANE DERIVATIVES FOR AUGMENTING OR ENHANCING THE FLAVOR OF FOODSTUFFS

This is a divisional of application Ser. No. 953,128, filed Oct. 20, 1978 now U.S. Pat. No. 4,195,099.

BACKGROUND OF THE INVENTION

The instant invention provides novel oxabicyclooctanes having the structure:

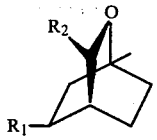

wherein $R_1$ is hydrogen or methyl and $R_2$ is one of $C_3$-$C_5$ alkyl or alkenyl as well as intermediates for producing same having the generic structure:

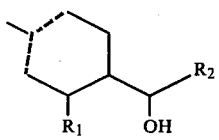

wherein $R_1$ is hydrogen or methyl, $R_2$ is one of $C_3$-$C_5$ alkyl or alkenyl and one of the dashed lines is a carbon-carbon double bond and the other of the dashed lines is a carbon-carbon single bond, and $C_1$-$C_3$ alkyl esters thereof, and used thereof for their organoleptic properties in consumable materials.

Chemical compounds which can provide green, minty, herbaceous (e.g., rosemary, garden mint, thyme and wet lettuce) cooling, sweet, fruity, woody, eucalyptol-like, buchu-like, caraway, spicey, carvone-like, minty, basil-like, sweet anise, peppery and geranium-like aromas with fruity, blueberry-like nuances are desirable in the art of perfumery. Many of the natural materials which provide such fragrances and contribute such desired nuances to perfumery compositions are high in cost, unobtainable at times, vary in quality from one batch to another and/or are generally subject to the usual variations of natural products.

By the same token, materials which can provide dill, parsley-like, nutmeg-like, celery-like, floral, lemon, grapefruit-like, carrot-like, raisin-like, woody, safranal-like, piney, strawberry-like, raspberry-like, blueberry-like, spicey, herbaceous, lime-like, black tea-like, black pepper-like, fennel, anise-like, licorice-like, green, sassafras-like, minty, juicy fruit, orange-like, sweet, floral, fruity, berry-like aromas and dill, parsley-like, nutmeg, celery-like, lemon, grapefruit-like, carrot-like, woody, raisin-like, tobacco-like, piney, spicey, strawberry-like, raspberry-like, blueberry-like, spicey, herbaceous, lime-like, black tea-like, black pepper, biting, sweet, fennel, anise-like, licorice-like, green, sassafras-like, minty, juicyfruit-like, orange-like, floral, fruity, berry-like and herbaceous flavor characteristics are desirable in applying the art of flavoring to foodstuffs, toothpastes, chewing gums and medicinal products. Many of the natural materials which provide such flavor notes and contribute desired nuances to flavoring compositions are high in cost, vary in quality from one batch to another and/or are generally subject to the usual variations of natural products.

By the same token, hay, fruity, herbaceous aromas prior to and on smoking are desirable in the tobacco art for enhancing natural tobacco-like notes.

There is, accordingly, a continuing effort to find synthetic materials which will replace, enhance or augment the essential flavor and fragrance notes provided by natural essential oils or compositions thereof. Unfortunately, many of these synthetic materials either have the desired nuances only to a relatively small degree or else contribute undesirable or unwanted odor to the compositions. The search for materials which can provide a more refined root beer-like flavor, for example, has been difficult and relatively costly in the areas of both natural products and synthetic products.

Artificial flavoring agents for foodstuffs have received increasing attention in recent years. For many years, such food flavoring agents have been preferred over natural flavoring agents at least in part due to their diminished cost and their reproducible flavor qualities. For example, natural food flavoring agents such as extracts, concentrates and the like are often subject to wide variations due to changes in quality, type and treatment of the raw materials. Such variations can be reflected in the end products and result in unfavorable flavor characteristics in said end product. Additionally, the presence of the natural product in the ultimate food may be undesirable because of increased tendency to spoil. This is particularly troublesome in food and food uses where such products as dips, soups, chips, sausages, gravies and the like are apt to be stored prior to use.

The fundamental problem in creating artificial flavor agents is that the artificial flavor to be achieved be as natural as possible. This generally proves to be a difficult task since the mechanism for flavor development in many foods, medicinal products, chewing gums and toothpastes is not completely known. This is noticeable in products having licorice, spice, dill, parsely, carrot, grapefruit, nutmeg, spearmint, lemon juice, lime, blueberry, raspberry, strawberry, black pepper, and root beer flavor characteristics, particularly.

Even more desirable are products that can serve to substitute for difficult-to-obtain natural perfumery oils and at the same time substitute for natural flavoring ingredients in foodstuffs, chewing gums, medicinal products and toothpastes and in addition, at the same time, substitute for natural flavoring ingredients in tobaccos.

Arctander in "Perfume and Flavor Chemicals (Aroma Chemicals)", Vol. I, 1969 at monograph No. 616 describes 1,8-cineole having the structure:

as being useful in perfumery and in flavor compositions.

Thus, Arctander states, regarding 1,8-cineole:

"Fresh, diffusive, camphoraceous-cool odor of poor tenacity. Sweet and fresh, cool-camphoraceous taste and cool mouthfeel unless very highly concentrated.

Widely used in perfume compositions for its refreshing effect in herbaceous type fragrances, Lavender, New Mown Hay, Fougere, etc. and in medicinal type odors for soap and household products. Also, in masking odors for industrial purposes, unless Eucalyptus oil must be used for its lower cost.

This oxide has found increased usage during the 1965/66 period of abnormally high prices for Lavandin and Spike Lavender oils.

The odor of Eucalyptus is, in some countries, rated synonomous with masking odors for lavatories, etc., a fact which has an unquestionable psychological effect, causing people to reject the odor of Eucalyptus for oral-hygienic purposes, etc. Similar viewpoints has been observed about the use of Methylsalicylate in dentrifrice in many European countries. Peculiarly enough, Methylsalicylate is still a popular candy-, soft-drink- and toothpaste flavor in the U.S.A., where the ester at the same time is used as a masking agent in toilet-bowl cleaners!

The 'olfactory association' is quite human and common, but it may at times completely destroy the chances of a chemical from its use in flavors or other field.

Eucalyptol is extensively used in flavor compositions, particularly in all types of preparations for oral hygiene, dentifrice, breath-sprays, mouthwashes, cough lozenges, pastilles, skin-rubbing lotions, inhalator fluids, etc.

It seems, however, that its use in skin rubbing lotions has hampered its popularity as a candy flavor in the U.S.A.

Normal use concentrations are about 1 to 15 ppm in the finished (flavored) product, but concentrations as high as 200 ppm are found in chewing gum."

Furthermore, the compound having the structure:

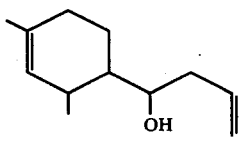

and the compound having the structure:

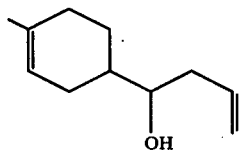

are reported by Sopov and Kovner at Zh. Obsch. Khim. 34, 1492-6 (1964) as abstracted in Chem. Abstracts, Vol. 61, 5529b.

The Sopov and Kovner reference does not, however, disclose organoleptic uses of the compounds having the structures:

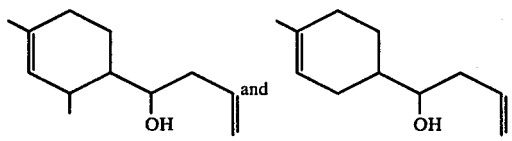

Furthermore, nothing in the prior art discloses any of the compounds having the generic structure:

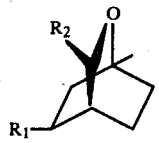

wherein $R_2$ is $C_3$-$C_5$ alkyl or alkenyl and $R_1$ is hydrogen or methyl and nothing in the prior art discloses organoleptic uses or uses as intermediates of the compound having the structure:

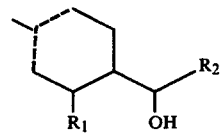

wherein $R_1$ is hydrogen or methyl and $R_2$ is $C_3$-$C_5$ alkyl or alkenyl, or lower alkyl esters thereof, e.g., acetates.

Insofar as their organoleptic uses are concerned, the compounds of the instant invention have unexpected, unobvious and advantageous properties over such compounds of the prior art as 1,8-cineole.

BRIEF DESCRIPTION OF THE DRAWINGS

FIG. 7 is the GLC profile for the product produced according to Example II.

FIG. 10 is the GLC profile for the product produced according to Example III.

FIG. 17 is the NMR spectrum for the product produced according to Example V(B).

FIG. 18 is the infra-red spectrum produced according to the process of Example V(B).

FIG. 25 is the GLC profile (5 hours) for the product produced according to Example VII(B).

FIG. 26 is the NMR spectrum for the product produced according to Example VII(B).

FIG. 29 is the NMR spectrum for the product produced according to Example VIII.

FIG. 30 is the infra-red spectrum for the product produced according to the process of Example VIII.

FIG. 31 is the GLC profile for the product produced according to the process of Example IX.

FIG. 32 is the NMR spectrum for the product produced according to the process of Example IX.

FIG. 35 is the NMR spectrum (fraction 7) for the product produced according to the process of Example X.

FIG. 36 is the infra-red spectrum (fraction 7) for the product produced according to the process of Example X.

FIG. 37 is the NMR spectrum for fraction 4 of the reaction product produced according to Example XXXII.

FIG. 38 is the infra-red spectrum for fraction 4 of the reaction product produced according to Example XXXII.

THE INVENTION

Figure 4:
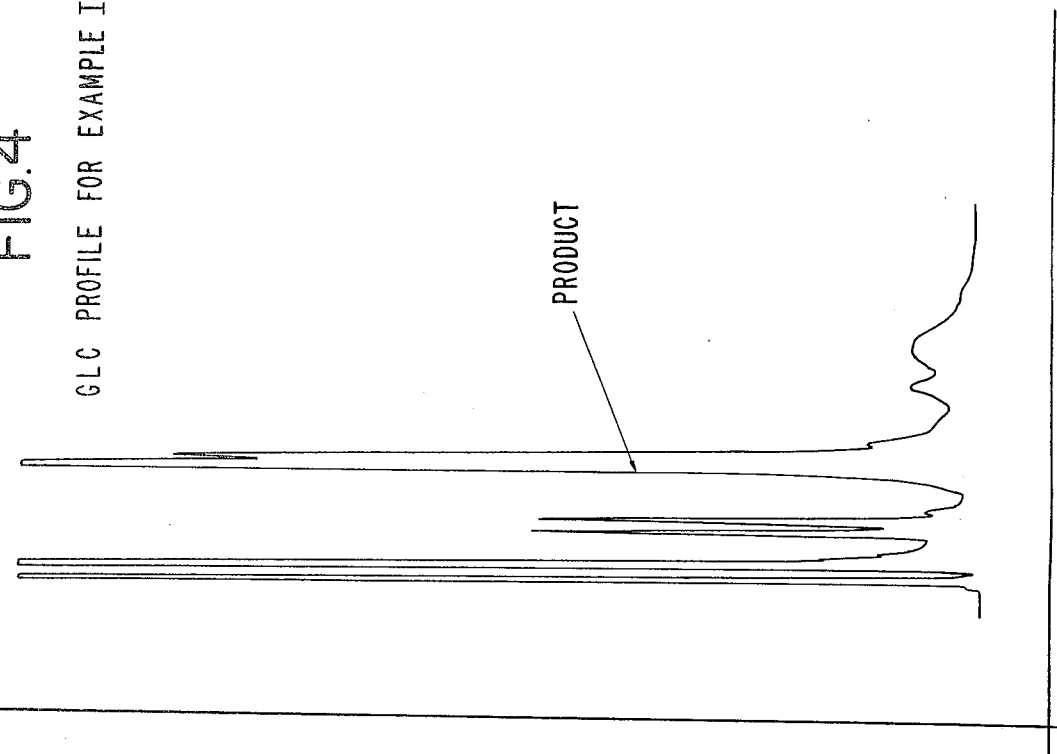
FIG. 4 is the GLC profile for the oxabicyclooctane produced according to Example IB.

It has now been determined that certain oxabicyclooctanes as well as certain precursors therefor which are cyclohexene alkyl and alkenyl carbinols and their esters are capable of imparting a variety of flavors and fragrances to various consumable materials and are also capable of augmenting or enhancing a variety of flavors and fragrances of various consumable materials.

Briefly, our invention contemplates augmenting or enhancing the flavors and/or fragrances of such consumable materials as perfumes, perfumed articles, colognes, foodstuffs, chewing gums, toothpastes, medicinal products and smoking tobaccos by adding thereto a small but effective amount of at least one of the compounds having one of the generic structures:

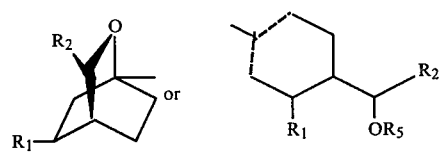

wherein $R_1$ is hydrogen or methyl; $R_2$ is $C_3$–$C_5$ alkyl or alkenyl; $R_5$ is hydrogen or $C_1$–$C_4$ acyl; and one of the dashed lines is a carbon-carbon single bond and the other of the dashed lines is a carbon-carbon double bond.

The oxabicyclooctane derivatives and the cyclohexene alkyl and alkenyl carbinols and esters thereof our invention augment or enhance dill, parsley, nutmeg, celery-like, floral, lemon, raisin-like, woody, saffranal-like, piney, strawberry-like, raspberry-like, blueberry-like, carrot-like, grapefruit-like, spicey, herbaceous, lime, black tea-like, black pepper, fennel, anise-like, licorice-like, green, sassafras-like, minty, juicyfruit, orange-like, sweet, floral, fruity, berry-like, and herbaceous aroma characteristics, and dill, parsley, nutmeg, celery-like, lemon, woody, raisin-like, carrot-like, grapefruit-like, tobacco-like, piney, spicey, strawberry-like, raspberry-like, blueberry-like, spicey, herbaceous, lime, black tea-like, black pepper, biting, sweet, fennel, anise-like, licorice-like, green, sassafras-like, minty, juicy-fruit-like, orange-like, floral, fruity, berry-like, and herbaceous flavor characteristics insofar as augmenting or enhancing the aroma or taste of foodstuffs, toothpastes, medicinal products and chewing gum.

The oxabicyclooctane derivatives and the cyclohexene alkyl and alkenyl carbinols and esters thereof of our invention also augment or enhance the green, minty, herbaceous (e.g., rosemary, garden mint, thyme and wet lettuce), cooling, sweet, fruity, woody, eucalyptol, buchu-like, caraway-like, spicey, carvone-like, basil-like, sweet anise-like, peppery and geranium aromas of perfumes, perfumed articles and colognes of our invention.

The oxabicyclooctane derivatives and the cyclohexene alkyl and alkenyl carbinols and esters thereof of our invention also augment or enhance the natural tobacco-like characteristics of smoking tobacco by imparting thereto hay, fruity and herbaceous aroma and taste nuances prior to and on smoking in the main stream and in the side stream.

Examples of the oxabicyclooctane derivatives and the cyclohexene alkyl and alkenyl carbinols and esters thereof our invention and their organoleptic characteristics are as follows:

| STRUCTURE OF COMPOUND | NAME OF COMPOUND | FLAVOR CHARACTERISTICS | FRAGRANCE CHARACTERISTICS |
|---|---|---|---|
|  | 1,5-Dimethyl-3-isopropyl-2-oxabicyclo[2.2.2]octane | A lime, lemon, rasin-like, woody, and saffronal-like aroma with lime, lemon, woody, rasin-like and tobacco-like flavor characteristics. | A green, minty, herbaceous (rosemary) aroma with a cooling effect. |
| 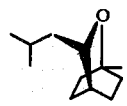 | 1-methyl-3-(2-methylpropyl)-2-oxabicyclo[2.2.2]octane | A dill, parsley-like, nutmeg-like, celery-like aroma with dill, parsley-like, nutmeg-like and celery-like flavor nuances. | |
| 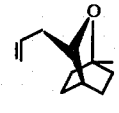 | 3-allyl-1-methyl-2-oxabicyclo[2.2.2]octane | A herbaceous, piney, spicey, strawberry-like, raspberry-like, and blueberry-like aroma characteristics with herbaceous, piney, spicey, strawberry-like, raspberry-like and blueberry-like flavor characteristics. | A minty, eucalyptol-like, herbaceous (garden mint, thyme), buchu-like aroma with caraway-like nuances. |
| 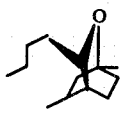 | 3-n-butyl-2,5-dimethyl-2-oxabicyclo[2.2.2]octane | A spicey, black pepper-like, herbaceous, lime and black tea aroma with spicey, black pepper-like, herbaceous, lime and black tea-like flavor nuances. | A green, spicey, carvone-like aroma. |
|  | 1,5-dimethyl-3-n-propyl-2-oxabicyclo[2.2.2]octane | A black pepper and spicey aroma with black pepper, spicey and biting flavor characteristics. | A herbaceous, minty (garden mint) aroma with basil, thyme and caraway nuances. |
| 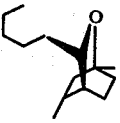 | 1,5-dimethyl-3-n-pentyl-2-oxabicyclo[2.2.2]octane | A woody, spicey and black pepper aroma with black pepper flavor characteristics insofar as foodstuffs are concerned. Insofar as tobacco uses are concerned, imparts a hay, fruity and herbaceous characteristic and enhances the natural tobacco notes prior to and on smoking insofar as smoking tobacco is concerned. | An oily, green, herbaceous (wet lettuce) aroma. |
| 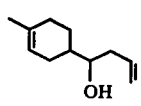 | α-allyl-4-methyl-3-cyclohexene-methanol | A sweet, fennel, anise-like, licorice-like and green aroma characteristic with sweet, fennel, anise-like, licorice-like and green flavor characteristics. | A sweet, anise, carvone-like and minty aroma. |
| 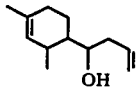 | 2,4-dimethyl-α-allyl-3-cyclohexenemethanol | A sweet, floral, licorice-like, fruity, berry-like, herbaceous, and green aroma with sweet, floral, licorice-like, fruity berry-like, herbaceous and green flavor characteristics. | A sweet, anisic, citrus aroma with minty, peppery, and geranium-like undertones. |
| 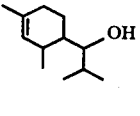 | 2,4-dimethyl-α-isopropyl-3-cyclohexene-1-methanol | A sassafras-like, minty, juicy fruit and orange-like aroma with sassafras-like, minty, juicy fruit-like and orange-like flavor characteristics. | |
| 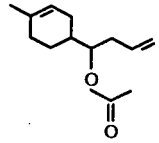 | α-allyl-4-methyl-3-cyclohexene-1-methanol acetate | A green, oriental, floral aroma character with green, floral and bitter flavor characteristics. | A sweet, fruity, herbaceous, floral aroma with carvone-like and geranyl acetate-like nuances. |

| STRUCTURE OF COMPOUND | NAME OF COMPOUND | FLAVOR CHARACTERISTICS | FRAGRANCE CHARACTERISTICS |
|---|---|---|---|
| | 4,6-dimethyl-α-allyl-3-cyclohexenemethanol | A sweet, floral, licorice-like, fruity, berry-like, herbaceous and green aroma characteristic with sweet, floral, licorice, fruity, berry, herbaceous and green flavor characteristics. | A sweet, herbaceous, fruity aroma with basil and blueberry-like undertones. |
| | α-allyl-4,6-dimethyl-3-cyclohexene-1-methanol acetate | A green, spicy, floral aroma characteristic with biting flavor characteristics at 2 ppm. | A green, fruity, anisic, woody aroma. |
| | | A weedy green, grapefruit-like, carrot-like aroma with a weedy green, grapefruit, carrot-like flavor at 3.0 ppm. | A green, floral, minty, lemonly aroma. |

The oxabicyclooctane derivatives and the cyclohexene alkyl and alkenyl carbinols and esters thereof of our invention can be produced by first forming a cyclohexene carboxaldehyde by reaction of an α,β-unsaturated aldehyde with a conjugated diene. The resulting cyclohexene carboxaldehyde is then reacted with a Grignard reagent to form an organometallic salt of a cyclohexene carbinol. The organometallic salt of the cyclohexene carbinol is then hydrolyzed (in the presence of acid) to form a cyclohexene carbinol of our invention. This reaction product may be used as is for its organoleptic properties or either (i) it may be further reacted by cyclizing the compound to form the desired 2-oxabicyclo[2.2.2]octane or (ii) it may be esterified with a $C_1$–$C_4$ acyl halide or acyl anhydride such as acetyl chloride or acetic anhydride. The over-all reaction sequence described above is as follows:

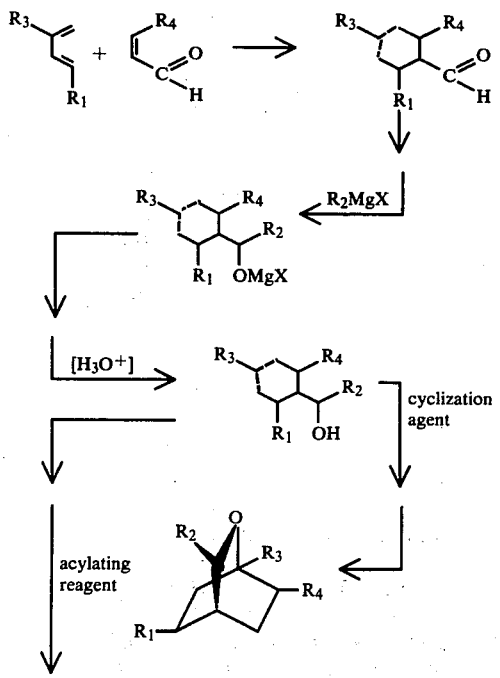

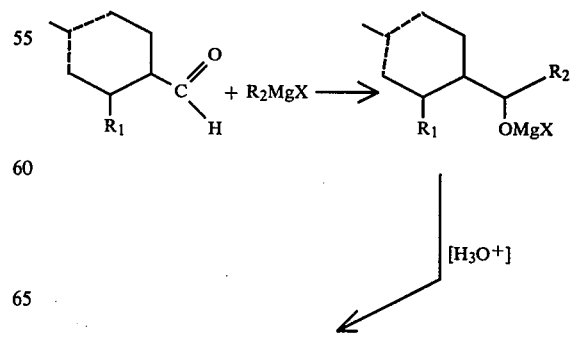

wherein $R_1$ and $R_3$ each represent hydrogen or methyl and are each the same or different; wherein $R_4$ is hydrogen, methyl or ethyl; wherein $R_2$ is one of $C_1$–$C_6$ alkyl or one of $C_3$–$C_5$ alkenyl; wherein $R_6$ is hydrogen, methyl or ethyl; and wherein one of the dashed lines is a carbon-carbon double bond and the other of the dashed lines is a carbon-carbon single bond; and where X is chloro, bromo or iodo.

The reaction scheme of our invention may be further exemplified and more specifically set forth insofar as it forms the novel compounds of our invention as follows:

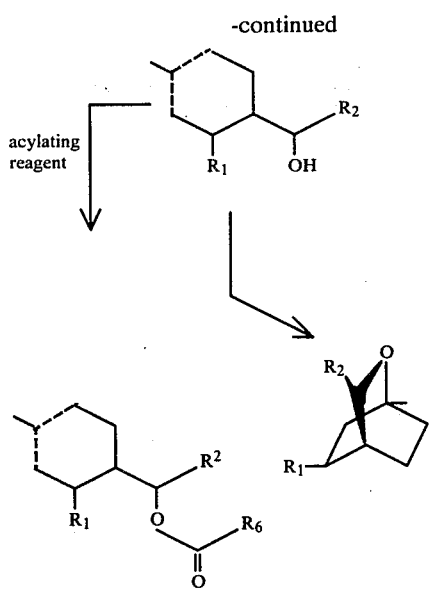

wherein one of the dashed lines is a carbon-carbon double bond and the other of the dashed lines is a carbon-carbon single bond; wherein $R_1$ is hydrogen or methyl; wherein $R_2$ is one of $C_3$-$C_5$ alkyl or alkenyl; wherein $R_6$ is hydrogen, methyl or ethyl; and wherein X is one of chloro, bromo or iodo.

The Diels-Alder reaction of the α,β-unsaturated aldehyde with the conjugated diene is a procedure well known in the prior art. The reaction may be carried out in the presence of Lewis acid catalysts such as zinc chloride, aluminum chloride or aluminum bromide; or it may be carried out in the absence of catalysts at higher temperatures, e.g., 50° C. up to 150° C. When carrying out the Diels-Alder reaction in the presence of catalysts, lower temperature, e.g., −10° C. up to 30° C. may be utilized.

That part of the reaction sequence whereby the cyclohexene carboxaldehyde is reacted with the Grignard reagent to form the cyclohexene carbinol organometallic salt followed by hydrolysis of the cyclohexene carbinol organometallic salt to form the cyclohexene carbinol followed by cyclization of the resulting cyclohexene carbinol to form the 2-oxabicyclo[2.2.2]octane may be carried out either in one step or in two steps.

In carrying out the "two-step reaction" whereby the cyclohexene carbinol is first isolated and then cyclized in the first step, that is, in the reaction of the Grignard reagent with the cyclohexene carboxaldehyde, the mole ratio of alkyl halide or alkenyl halide to magnesium in order to form the Grignard reagent is from 0.9:1 up to 1.5:1. The mole ratio of alkyl halide or alkenyl halide to cyclohexene carboxaldehyde is from 0.8:1 up to 1.5:1. This reaction of the Grignard reagent with the cyclohexene carboxaldehyde takes place in an ether solvent such as diethyl ether, tetrahydrofuran or di-n-butyl ether or another inert solvent such as toluene, chloroform or benzene to which two equivalents of ether has been added. The temperature of reaction preferably is between 0° and 100° C. with the most preferred temperature range for this reaction being from 35° C. up to 45° C.

In the two-step reaction, the resulting cyclohexene carbinol is then isolated as by distillation. The resulting cyclohexene carbinol is then cyclized at a temperature in the range of from 25° C. up to 150° C. in the presence of an acid such as aqueous hydrochloric acid or sulfuric acid or phosphoric acid. This acid may be used in combination with an alcohol such as isopropyl alcohol or with some other solvents such as tetrahydrofuran or acrylonitrile or the acid may be used by itself to effect the cyclization. The cyclization in the alternative may be carried out using a Lewis Acid such as borotrifluoride, aluminum trichloride, zinc chloride, stannic chloride, or zinc bromide in the presence of a solvent such as toluene, chloroform or xylene.

As stated above, the reaction of the cyclohexene carboxaldehyde to form the cyclohexene carbinol followed by cyclization may take place in a single reactor without separation of the cyclohexene carbinol. The conditions are the same as stated above for the two-step reaction.

If desired, the cyclohexene carbinol may be acylated rather than cyclized whereby esters useful for their organoleptic properties are formed. Suitable acrylating reagents are acidic anhydride, acetyl chloride, propionic anhydride and propionyl chloride. The acylation is carried out under standard acylating conditions known to those having ordinary skill in the art, e.g., −10° C.-50° C. in the presence in an inert solvent, e.g., toluene or xylene.

The individual oxabicyclooctane derivatives and the cyclohexene alkyl and alkenyl carbinols and esters of our invention can be obtained in pure form or in substantially pure form by conventional purification techniques. Thus, the products can be purified and/or isolated by distillation, extraction, crystallization, preparative chromatographic techniques (column chromatography and vapor phase chromatography) and the like. It has been found desirable to purify the oxacyclooctane derivatives and the cyclohexene alkyl and alkenyl carbinols and esters of our invention by fractional distillation in vacuo.

When the oxabicyclooctane derivatives and the cyclohexene alkyl and alkenyl carbinols and esters of our invention are used as food flavor adjuvants, the nature of the co-ingredients included with said oxabicyclooctane derivatives and the cyclohexene alkyl and alkenyl carbinols and esters in formulating the product composition will also serve to alter, modify, augment or enhance the organoleptic characteristics of the ultimate foodstuff treated therewith.

As used herein in regard to flavors, the terms "alter", "modify" and "augment" in their various forms means "supplying or imparting flavor character or note to otherwise bland, relatively tasteless substances or augmenting the existing flavor characteristic where a natural flavor is deficient in some regard or supplementing the existing flavor impression to modify its quality, character or taste".

The term "enhance" is used herein to mean the intensification of a flavor or aroma characteristic or note without the modification of the quality thereof. Thus, "enhancement" of a flavor or aroma means that the enhancement agent does not add any additional flavor note.

As used herein, the term "foodstuff" includes both solid and liquid ingestible materials which usually do, but need not, have nutritional value. Thus, foodstuffs include soups, convenience foods, beverages, dairy products, candies, vegetables, cereals, soft drinks, snacks, and the like.

As used herein, the term "medicinal product" includes both solids and liquids which are ingestible, non-toxic materials which have medicinal value such as cough syrups, cough drops, aspirin and chewable medicinal tablets.

The term "chewing gum" is intended to mean a composition which comprises a substantially water insoluble, chewable plastic gum base such as chicle, or substitutes therefor, including jelutong, guttakay, rubber or certain comestible natural or synthetic resins or waxes. Incorporated with the gum base in admixture therewith may be plasticizers or softening agents, e.g., glycerine, and a flavoring composition which incorporates one or more of the oxabicyclooctane derivatives and the cyclohexene alkyl and alkenyl carbinols and esters of our invention, and in addition, sweetening agents which may be sugars, including sucrose or dextrose and/or artificial sweeteners such as cyclamates or saccharin. Other optional ingredients may also be present.

Substances suitable for use herein as co-ingredients or flavoring adjuvants are well known in the art for such use, being extensively described in the relevant literature. It is a requirement that any such material be "ingestibly" acceptable and thus non-toxic and otherwise non-deleterious particularly from an organoleptic standpoint whereby the ultimate flavor and/or aroma of the consumable material used is not caused to have unacceptable aroma and taste nuances. Such materials may in general be characterised as flavoring adjuvants or vehicles comprising, broadly, stabilizers, thickeners, surface active agents, conditioners, other flavorants and flavor intensifiers.

Stabilizer compounds include preservatives, e.g., sodium chloride, antioxidants, e.g., calcium and sodium ascorbate, ascorbic acid, butylated hydroxyanisole (mixture of 2- and 3-tertiary-butyl-4-hydroxy anisole), butylated hydroxytoluene (2,6-di-tertiary-butyl-4-methyl phenol), propyl gallate and the like, and sequestrants, e.g., citric acid.

Thickener compounds include carriers, binders, protective colloids, suspending agents, emulsifiers and the like, e.g., agar agar, carrageenan; cellulose and cellulose derivatives such as carboxymethyl cellulose and methyl cellulose; natural and synthetic gums such as gum arabic, gum tragacanth; gelatin, proteinaceous materials; lipids, carbohydrates; starches, pectins, and emulsifiers, e.g., mono- and diglycerides of fatty acids, skim milk powder, hexoses, pentoses, disaccharides, e.g., sucrose, corn syrup and the like.

Surface active agents include emulsifying agents, e.g., fatty acids such as capric acid, caprylic acid, palmitic acid, myristic acid and the like, mono- and diglycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g., benzoyl peroxide, calcium peroxide, hydrogn peroxide and the like; starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like; colorants, e.g., carminic acid, cochineal, tumeric and curcuma and the like, firming agents such as aluminum sodium sulfate, calcium chloride and calcium gluconate; texturizers, anti-caking agents, e.g., aluminum calcium sulfate and tri-basic calcium phosphate; enzymes; yeast foods, e.g., calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include organic acids, e.g., acetic acid, formic acid, 2-hexenoic acid, benzoic acid, n-butyric acid, caproic acid, caprylic acid, cinnamic acid, isobutyric acid, isovaleric acid, alphamethylbutyric acid, propionic acid, valeric acid, 2-methyl-2-pentenoic acid, and 2-methyl-3-pentenoic acid; ketones and aldehydes, e.g., acetaldehyde, acetophenone, acetone, acetyl methyl carbinol, acrolein, n-butanal, crotonal, diacetyl, 2-methylbutanal, beta,-beta-dimethyl acrolein; methyl n-amyl ketone, n-hexanal, 2-hexenal, isopentanal, hydrocinnamic aldehyde, cis-3-hexenal, 2-heptenal, nonyl aldehyde, 4-(p-hydroxyphenyl)-2-butanone, alpha-ionone, beta-ionone, 2-methyl-3-butanone, benzaldehyde, beta-damascone, alpha-damascone, beta-damascenone, acetophenone, 2-heptanone, o-hydroxy-acetophenone, 2-methyl-2-hepten-6-one, 2-octanone, 2-undecanone, 3-phenyl-4-pentenal, 2-phenyl-2-hexenal, 2-phenyl-2-pentenal, furfural, 5-methylfurfural, cinnamaldehyde, beta-cyclohomocitral, 2-pentanone, 2-pentenal and propanal; alcohols such as 1-butanol, benzyl alcohol, 1-borneol, trans-2-buten-1-ol, ethanol, geraniol, 1-hexanol, 2-heptanol, trans-2-hexenol-1, cis-3-hexen-1-ol, 3-methyl-3-buten-1-ol, 1-pentanol, 1-penten-3-ol, p-hydroxyphenyl-2-ethanol, isoamyl alcohol, isofenchyl alcohol, phenyl-2-ethanol, alpha-terpineol, cis-terpinhydrate, eugenol, linalool, 2-heptanol, acetoin; esters, such as butyl acetate, ethyl acetate, ethyl acetoacetate, ethyl benzoate, ethyl butyrate, ethyl caprate, ethyl caproate, ethyl carpylate, ethyl cinnamate, ethyl crotonate, ethyl formate, ethyl isobutyrate, ethyl isovalerate, ethyl laurate, ethyl myristate, ethyl alpha-methylbutyrate, ethyl propionate, ethyl salicylate, trans-2-hexenyl acetate, hexyl acetate, 2-hexenyl butyrate, hexyl butyrate, isoamyl acetate, isopropyl butyrate, methyl acetate, methyl butyrate, methyl caproate, methyl isobutyrate, alpha-methylphenylglycidate, ethyl succinate, isobutyl cinnamate, cinnamyl formate, methyl cinnamate, and terpenyl acetate; hydrocarbons such as dimethyl naphthalene, dodecane, methyldiphenyl, meythyl naphthalene, myrcene, naphthalene, octadecane, tetradecane, tetramethylnaphthalene, tridecane, trimethylnaphthalene, undecane, caryophyllene, alphaphellandrene, beta-phellandrene, p-cymene 1-alpha-pinene, beta-pinene, dihydrocarveol; pyrazines such as 2,3-dimethylpyrazine, 2,5-dimethylpyrazine, 2,6-dimethylpyrazine, 3-ethyl-2,5-dimethylpyrazine, 2-ethyl-3,5,6-trimethylpyrazine, 3-isoamyl-2,5-dimethylpyrazine, 5-isoamyl-2,3-dimethylpyrazine, 2-isoamyl-3,5,6-trimethylpyrazine, isopropyl dimethylpyrazine, methyl ethylpyrazine, tetramethylpyrazine, trimethylpyrazine; essential oils such as jasmine absolute, cassia oil, cinnamon bark oil, black pepper oleoresin, oil of black pepper, rose absolute, orris absolute, oil of cubeb, oil of coriander, oil of pimento leaf, oil of patchouli, oil of nutmeg, lemon essential oil, safran oil, Bulgarian rose, capsicum, yara yara and vanilla; lactones such as γ-nonalactone; sulfides, e.g., methyl sulfide and other materials such as maltol, and acetals (e.g., 1,1-diethoxyethane, 1,1-dimethyloxyethane and dimethoxymethane), piperine, chavicine, and piperidine.

The specific flavoring adjuvant selected for use may be either solid or liquid depending upon the desired physical form of the ultimate product, i.e., foodstuff, whether simulated or natural, and should, in any event, (i) be organoleptically compatable with the oxabicyclooctane derivatives and the cyclohexene alkyl and alkenyl carbinols and esters of our invention by not covering or spoiling the organoleptic properties (aroma and/or taste) thereof; (ii) be non-reactive with the oxabicyclooctene derivatives and the cyclohexene alkyl and alkenyl carbinols and esters of our invention and (iii) be capable of providing an environment in which the oxabicyclooctane derivatives and the cyclohexene alkyl and alkenyl carbinols and esters can be dispersed or admixed to provide a homogeneous medium. In addition, selection of one or more flavoring adjuvants, as well as the quantities thereof will depend upon the precise organoleptic character desired in the finished product. Thus, in the case of flavoring compositions, ingredient selection will vary in accordance with the foodstuff, chewing gum, medicinal product or toothpaste to which the flavor and/or aroma are to be imparted, modified, altered or enhanced. In contradistinction, in the preparation of solid products, e.g., simulated foodstuffs, ingredients capable of providing normally solid compositions should be selected such as various cellulose derivatives.

As will be appreciated by those skilled in the art, the amount of oxabicyclooctane derivatives and the cyclohexene alkyl and alkenyl carbinols and esters employed in a particular instance can vary over a relatively wide range, depending upon the desired organoleptic effects to be achieved. Thus, correspondingly, greater amounts would be necessary in those instances wherein the ultimate food composition to be flavored (e.g., with a spice flavor or a specific black pepper-like flavor) is relatively bland to the taste, whereas relatively minor quantities may suffice for purposes of enhancing the composition merely deficient in natural flavor or aroma. The primary requirement is that the amount selected be effective, i.e., sufficient to alter, modify or enhance the organoleptic characteristics of the parent composition, whether foodstuff per se, chewing gum per se, medicinal product per se, toothpaste per se, or flavoring composition.

The use of insufficient quantities of oxabicyclooctane derivatives and the cyclohexene alkyl and alkenyl carbinols and esters will, of course, substantially vitiate any possibility of obtaining the desired results while excess quantities prove needlessly costly and in extreme cases may disrupt the flavor-aroma balance, thus proving selfdefeating. Accordingly, the terminology "effective amount" and "sufficient amount" is to be accorded a significance in the context of the present invention consistent with the obtention of desired flavoring effects.

Thus, and with respect to ultimate food compositions, chewing gum compositions, medicinal product compositions and toothpaste compositions, it is found that quantities of bicyclooctane derivatives and the cyclohexene alkyl and alkenyl carbinols and esters ranging from a small but effective amount, e.g., 0.05 parts per million up to about 500 parts per million based on total composition, are suitable. Concentrations in excess of the maximum quantity stated are not normally recommended since they fail to provide commensurate enhancement of organoleptic properties. In those instances wherein the bicyclooctane derivatives and the cyclohexene alkyl and alkenyl carbinols and esters are added to the foodstuff as an integral component of a flavoring composition, it is of course, essential that the total quantity of flavoring composition employed be sufficient to yield an effective bicyclooctane derivative and cyclohexene alkyl and alkenyl carbinol and ester concentration in the foodstuff product.

Food flavoring compositions prepared in accordance with the present invention preferably contain the bicyclooctane derivatives and cyclohexene alkyl and alkenyl carbinols and esters in concentrations ranging from about 0.025% up to about 15% by weight based on the total weight of the said flavoring composition.

The composition described herein can be prepared according to conventional techniques well known as typified by cake batters and fruit drinks and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing the bicyclooctane derivatives and cyclohexene alkyl and alkenyl carbinols and esters with, for example, gum arabic, gum tragacanth, carrageenan and the like, and thereafter spray-drying the resultant mixture whereby to obtain the particular solid product. Pre-prepared flavor mixes in powder form, e.g., a fruit-flavored powder mix, are obtained by mixing the dried solid components, e.g., starch, sugar and the like, and bicyclooctane derivatives and cyclohexene alkyl and alkenyl carbinols and esters in a dry blender until the requisite degree of uniformity is achieved.

It is presently preferred to combine with the bicyclooctane derivatives and cyclohexene alkyl and alkenyl carbinols and esters of our invention, the following adjuvants: Oil of Cubeb; Phellandrene; $\beta$-Phellandrene; Oil of Coriander; Oil of Pimento Leaf, Oil of Patchouli; Natural Lemon Oil; Acetaldehyde; $\alpha$-Terpineol; Citral; Carvone; Terpinolene; $\alpha$-Terpinene; Diphenyl; $\alpha$-Fenchyl Alcohol; Cineole; Limonene; Linalool; Geranyl Acetate; Nootkatone; Neryl Acetate; Heliotropin; Maltol, Vanillin; Ethyl Maltol; Ethyl Vanillin; Anisaldehyde; Alpha Pinene; Beta-Pinene; Beta-Caryophyllene; Dihydrocarveol; Piperonal; Piperine; Chavicine; Piperidine; Oil of Black Pepper; Black Pepper Oleoresin; Capsicum; Oil of Nutmeg; Cardamon Oil; Clove Oil; Separmint Oil; Oil of Peppermint; and $C_{10}$-Terpinyl Ethers as described in Application for U.S. Letters Patent, Ser. No. 872,937 filed on Jan. 27, 1978, now U.S. Pat. No. 4,131,687 issued on Dec. 26, 1978 (such as fenchyl ethyl ethers).

The oxabicyclooctane derivatives and the cyclohexene alkyl and alkenyl carbinols and esters of our invention can be used to contribute green, minty, herbaceous (e.g., rosemary, garden mint, thyme, wet lettuce), sweet, fruity, woody, minty, cooling-like, eucalyptol-like, buchu-like, caraway, spicey, carvone-like, basil-like, anise-like, citrus aromas with minty, peppery and geranium-like and basil-blueberry-like undertones to perfumes, perfumed articles and colognes. As olfactory agents, the oxabicyclooctane derivatives and the cyclohexene alkyl and alkenyl carbinols and esters of our invention can be formulated into or used as components of a "perfume composition" or can be used as components of a "perfumed article" or the perfume composition may be added to perfumed articles.

The term "perfume composition" is used herein to mean a mixture of organic compounds including, for example, alcohols, aldehydes, ketones, nitriles, ethers, lactones, natural essential oils, synthetic essential oils and frequently hydrocarbons which are admixed so that the combined odors of the individual components produce a pleasant or desired fragrance. Such perfume compositions usually contain: (a) the main note or the "bouquet" or foundation-stone of the composition; (b) modifiers which round-off and accompany the main note; (c) fixatives which include odorous substances which lend a particular note to the perfume throughout all stages of evaporation, and substances which retard evaporation; and (d) top-notes which are usually low-boiling, fresh-smelling materials.

In perfume compositions, the individual component will contribute its particular olfactory characteristics, but the overall effect of the perfume composition will be the sum of the effects of each of the ingredients. Thus, the individual compounds of this invention, or mixtures thereof, can be used to alter the aroma characteristics of a perfume composition, for example, by highlighting or moderating the olfactory reaction contributed by another ingredient in the composition.

The amount of the oxabicyclooctane derivatives and/or the cyclohexene alkyl and alkenyl carbinols and/or esters of this invention which will be effective in perfume compositions depends on many factors, including the other ingredients, their amounts and the effects which are desired. It has been found that perfume compositions containing as little as 0.5% of the oxabicyclooctane derivatives and the cyclohexene alkyl and/or alkenyl carbinols and/or esters of this invention, or even less, can be used to impart an interesting minty, herbaceous and/or anise-like aroma to soaps, liquid and solid cationic, anionic and nonionic detergents, cosmetics, powders, liquid and solid fabric softeners, optical brightener compositions, and other products. The amount employed can range up to 50% or higher and will depend on considerations of cost, nature of the end product, and the effect desired on the finished product and particular fragrance sought.

The oxabicyclooctane derivatives and the cyclohexene alkyl and alkenyl carbinols and esters of this invention can be used alone or in a perfume composition as an olfactory component in detergents and soaps, space odorants and deodorants; perfumes; colognes, toilet waters; bath salts; hair preparations such as lacquers, brilliantines, pomades, and shampoos; cosmetic preparations such as creams, deodorants, hand lotions, and sun screens; powders such as talcs, dusting powders, face powder, and the like. When used as an olfactory component of a perfumed article, as little as 0.01% of one or more of the oxabicyclooctane derivatives and/or cyclohexene alkyl and alkenyl carbinols and/or esters will suffice to impart an interesting minty, herbaceous and/or anise-like aroma. Generally, no more than 0.5% is required.

In addition, the perfume composition can contain a vehicle or carrier for the oxabicyclooctane derivatives and the cyclohexene alkyl and alkenyl carbinols and esters alone or with other ingredients. The vehicle can be a liquid such as an alcohol such as ethanol, a glycol such as propylene glycol, or the like. The carrier can be an absorbent solid such as a gum or components for encapsulating the composition such as gelatin which can be used to form a capsule wall surrounding the perfume oil, by means of coacervation.

An additional aspect of our invention provides an organoleptically improved smoking tobacco product and additives therefor including methods of making the same which overcome problems heretofore encountered in the creation or enhancement of specific desired natural tobacco-like notes, particularly hay-like notes. Such notes, both prior to and on smoking, in both the main stream and the side stream, may now be readily controlled and maintained at the desired uniform level regardless of variations in the tobacco components of the blend; or the nature of the filter used in conjunction with the smoking tobacco article.

This invention further provides improved tobacco additives and additives for materials used in the fabrication of tobacco articles (particularly smoking tobacco articles) and methods whereby desirable hay-like notes may be imparted to smoking tobacco products and may be readily varied and controlled to produce the desired uniform flavoring characteristics.

In carrying out this aspect of our invention, we add to smoking tobacco materials or a suitable substitute therefor (e.g., dried lettuce leaves) an aroma and flavor additive containing as an active ingredient, one or more of the oxabicyclooctane derivatives and/or the cyclohexene alkyl and alkenyl carbinols and/or esters of our invention.

In addition to the oxabicyclooctane derivatives and the cyclohexene alkyl and alkenyl carbinols and esters of our invention, other flavoring and aroma additives may be added to the smoking tobacco material or substitute therefor either separately or in mixture with one or more of the oxabicyclooctane derivatives and/or the cyclohexene alkyl and alkenyl carbinols and/or esters of our invention:

I. Synthetic Materials

Beta-methylcinnamaldehyde;
Eugenol;
Dipentene;
Damascenone;
Maltol;
Ethyl maltol;
Delta-undecalactone;
Delta-decalactone;
Benzaldehyde;
Amyl acetate;
Ethyl butyrate;
Ethyl valerate;
Ethyl acetate;
2-Hexen-1-ol;
2-Methyl-5-isopropyl-1,3-nonadiene-8-one;
2-Methyl-5-isopropylacetophenone;
2-Hydroxy-2,5,5,8α-tetramethyl-1-)2-hydroxyethyl)-decahydronaphthalene;
Dodecahydro-3α,6,6,9α-tetramethylnaphtho-(2,1-$\beta$)-furan;
4-Hydroxyhexenoic acid, gamma-lactone;
Polyisoprenoid hydrocarbons defined in Example V of U.S. Pat. No. 3,589,372 issued on June 29, 1971

II. Natural Oils

Celery seed oil;
Coffee extract;
Bergamot oil;
Cocoa extract;
Nutmeg oil;
Origanum oil.

An aroma and flavoring concentrate containing one or more of the oxabicyclooctane derivatives and/or the cyclohexene alkyl and alkenyl carbinols and/or esters of our invention and, if desired, one or more of the above-indicated additional flavoring additives may be added to the smoking tobacco material, to the filter or to the leaf or paper wrapper or to a filter which is part of the smoking article. The smoking tobacco material may be shredded, cured, cased and blended tobacco material or reconstituted tobacco material or tobacco substitutes (e.g., lettuce leaves) or mixtures thereof. The proportions of flavoring additives may be varied in accordance with taste, but insofar as enhancement or the imparting of hay-like notes prior to and on smoking, in both the main stream and the side stream, we have found that satisfactory results are obtained if the proportion by weight of the sum total of oxabicyclooctane derivatives and/or the cyclohexene alkyl and alkenyl carbinols and/or esters to smoking tobacco material is between 50 ppm and 1500 ppm (0.005%-0.15%) of the active ingredients to the smoking tobacco material. We have further found that satisfactory results are obtained if the proportions by weight of the sum total of oxabicyclooctane derivatives and/or cyclohexene alkyl and alkenyl carbinols and/or esters used to flavoring material is between 0.05:1 and 0.50:1.

Any convenient method for incorporating the oxabicyclooctane derivatives and cyclohexene alkyl and alkenyl carbinols and esters in the tobacco product may be employed. Thus the oxabicyclooctane derivatives and cyclohexene alkyl and alkenyl carbinols and esters taken alone or along with other flavoring additives may be dissolved in a suitable solvent such as food grade ethanol, pentane, diethyl ether and/or other volatile organic solvents, and the resulting solution may either be sprayed on the cured, cased and blended tobacco material; or the tobacco material or filter may be dipped into such solution. Under certain circumstances, a solution of one or more oxabicyclooctane derivatives and/or cyclohexene alkyl and alkenyl carbinols and/or esters taken alone or taken further together with other flavoring additives as set forth above, may be applied by means of a suitable applicator such as a brush or roller on the paper or leaf wrapper for the smoking product, or it may be applied to the filter by either spraying or dipping or coating.

Furthermore, it will be apparent that only a portion of the tobacco or substitute therefor need be treated, and the thus-treated tobacco may be blended with other tobaccos before the ultimate tobacco product is formed. In such cases, the tobacco treated may have one or more oxabicyclooctane derivatives and/or cyclohexene alkyl and alkenyl carbinols and/or esters of our invention in excess of the amounts or concentrations above indicated so that when blended with other tobaccos, the final product will have the percentage within the indicated range.

While our invention is particularly useful in the manufacture of smoking tobacco such as cigarette tobacco, cigar tobacco and pipe tobacco, other tobacco products formed from sheeted tobacco dust or fines may also be used. As stated supra, the oxabicyclooctane derivatives and cyclohexene alkyl and alkenyl carbinols and esters of our invention can be incorporated with materials such as filter tip materials, seam paste, packaging materials and the like which are used along with the tobacco to form a product adapted for smoking. Furthermore, the oxabicyclooctane derivatives and cyclohexene alkyl and alkenyl carbinols and esters of our invention can be added to certain tobacco substitutes of natural or synthetic origin (e.g., dried lettuce leaves) and, accordingly, by the term "tobacco" as used throughout this specification is meant any composition intended for human consumption, by smoking or otherwise, whether composed of tobacco plant parts or substitute materials or both.

It will thus be apparent that the oxabicyclooctane derivatives and cyclohexene alkyl and alkenyl carbinols and esters of our invention can be utilized to alter, modify, augment or enhance sensory properties, particularly organoleptic properties, such as flavor(s) and/or fragrance(s) of a wide variety of consumable materials.

The following examples serve to illustrate our invention, and this invention is to be considered restricted thereto only as indicated in the appended claims.

All parts and percentages given herein are by weight unless otherwise specified.

EXAMPLE I

Reaction:

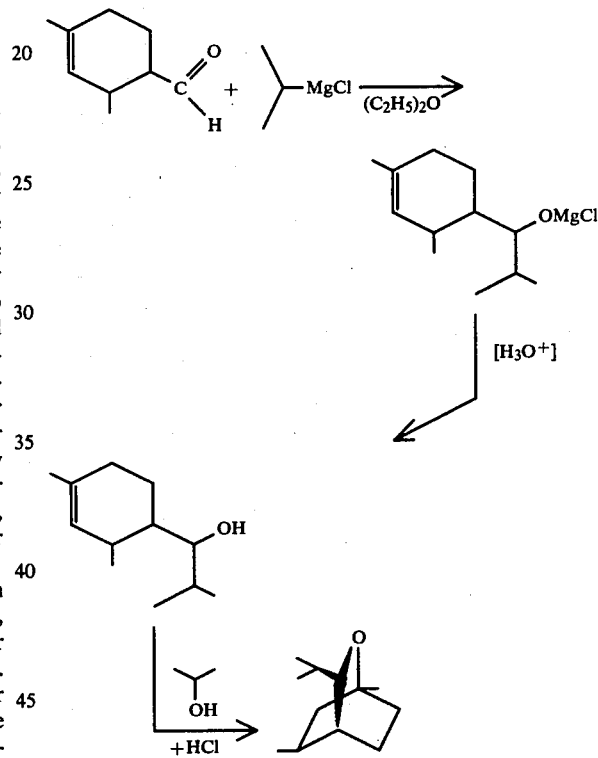

Part 1A: Preparation of 2,4-Dimethyl-Alpha-Isopropyl-3-Cyclohexene-1-Methanol

A solution of isopropyl magnesium chloride in ether is prepared by dropwise adding a solution of 164 grams (2.1 moles) of 2-chloropropane in 200 ml of ether to a stirred slurry of 50 grams (2.1 moles) of magnesium in 500 ml of ether at reflux under nitrogen. The resulting solution is stirred at reflux for 30 minutes. A solution of 164 grams (2 moles) of 2,4-dimethyl-3-cyclohexenecarboxaldehyde in 200 ml of ether is added over a 45-minute period to the reaction mixture at reflux under nitrogen. The resulting slurry is heated at reflux for 30 minutes and then cooled to 0° C. 400 ml of 18% aqueous hydrochloric acid is slowly added with cooling and stirring. Two clear layers are formed. The aqueous layer is discarded and the organic layer is washed twice with $H_2O$, neutralizing the second wash with aqueous caustic soda. The ether is removed by distillation at atmospheric pressure. Fractional distillation of the remaining oil (375 grams) through a 1½"×12" Goodloe packed column affords 121 grams of recovered 2,4-dimethyl-3-cyclohexenecarboxaldehyde; 54 grams of 1,5-dimethyl-3-isopropyl-2-oxabicyclo[2.2.2]octane; and 173 grams of 2,4-dimethylalpha-isopropyl-3-cyclohexene-1-methanol (b.p. 91° C., 2.1 mm Hg pressure).

Figure 1:
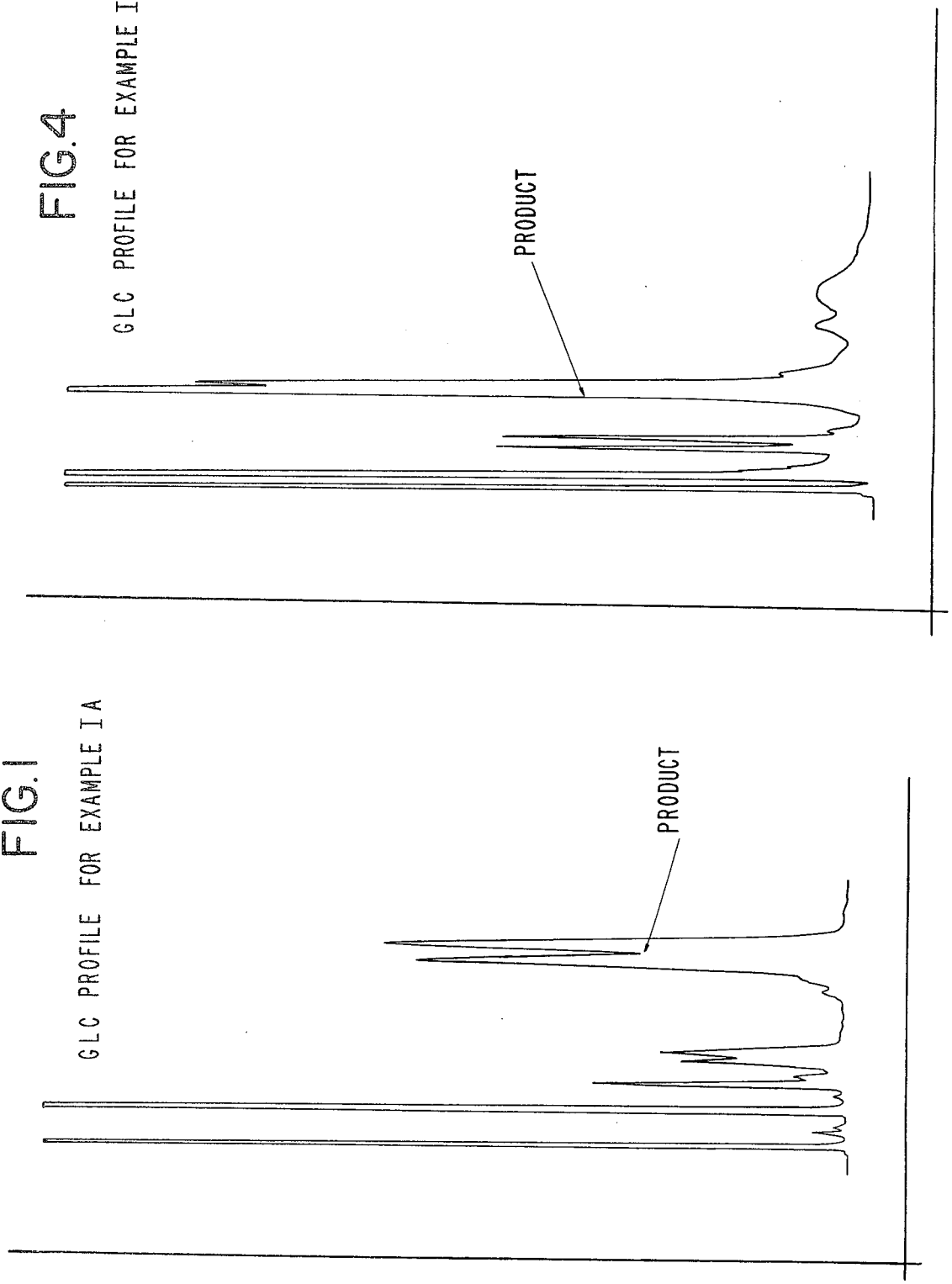
FIG. 1 is the GLC profile for the product produced according to Example IA.
Figure 2:
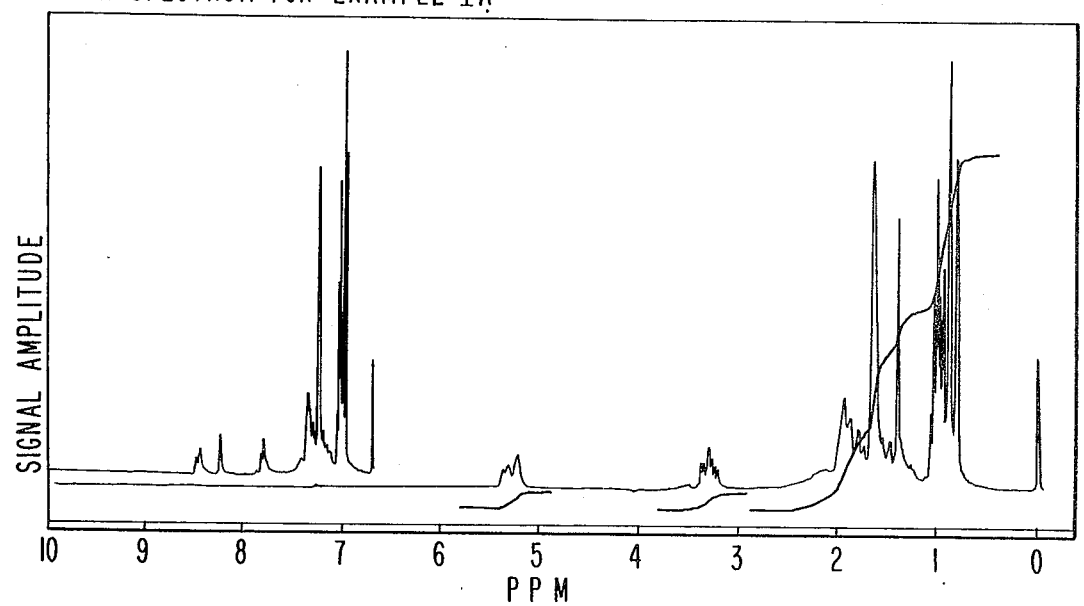
FIG. 2 is the NMR spectrum for the product produced according to Example IA.
Figure 3:
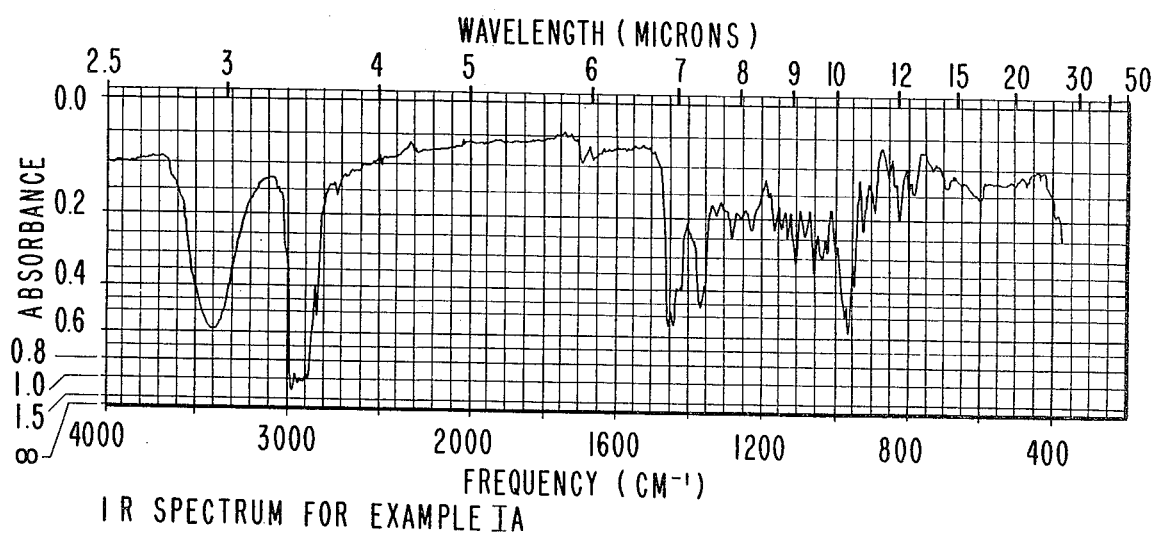
FIG. 3 is the infra-red spectrum for the product produced according to Example IA.

The GLC profile for the reaction mass is set forth in FIG. 1. The NMR spectrum for fraction 12 is set forth in FIG. 2. The infra-red spectrum for fraction 12 is set forth in FIG. 3. The NMR and IR spectra confirm that the resulting product is 2,4-dimethyl-alphaisopropyl-3-cyclohexene-1-methanol.

Part IB: Preparation of 1,5-Dimethyl-3-Isopropyl-2-Oxabicyclo[2.2.2]Octane

A solution of 130 grams of 2,4-dimethyl-alpha-isopropyl-3-cyclohexene methanol, 300 grams of isopropyl alcohol and 1000 ml of concentrated HCl is heated 2½ hours at reflux. The reaction mass is cooled and 1500 ml of H₂O and 100 ml of toluene is added with stirring. The aqueous layer is discarded and the organic layer is washed twice with water, neutralizing with aqueous caustic soda on the second wash. The organic layer is distilled through a 48" Vigreux column affording 25 grams of 1,5-dimethyl-3-isopropyl-2-oxabicyclo[2.2.2]octane (b.p. 55° C., 1.8 mm Hg pressure).

The NMR and IR spectra is taken from fraction 5 of the distillation.

Figure 5:
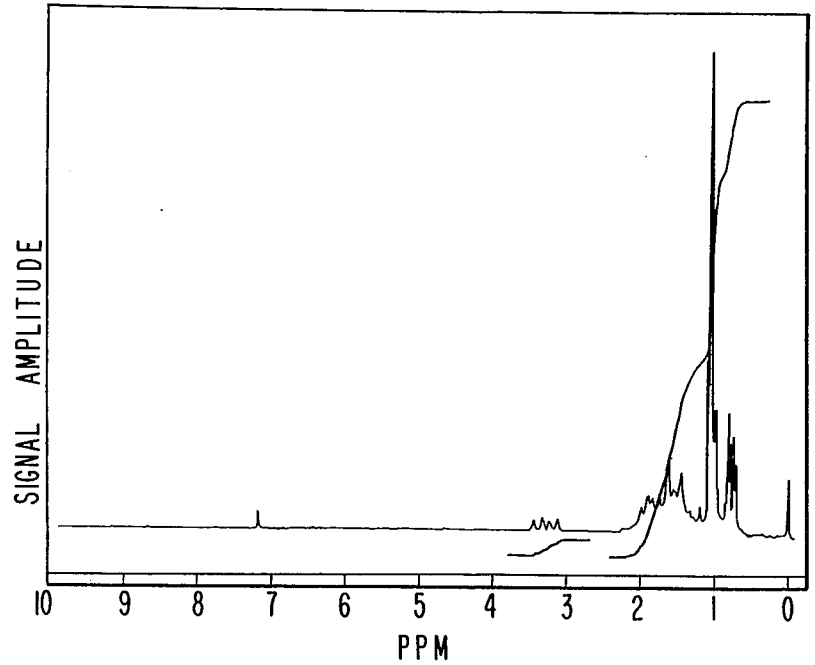
FIG. 5 is the NMR spectrum for the product produced according to Example IB.
Figure 6:
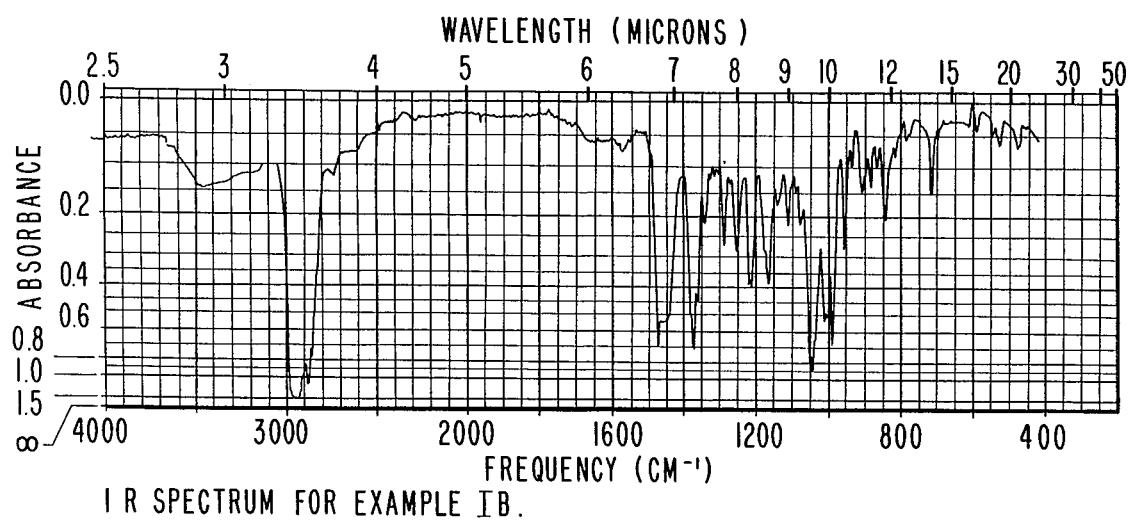
FIG. 6 is the infra-red spectrum for the product produced according to Example IB.

FIG. 4 is the GLC profile for the reaction product of this Example IB. FIG. 5 is the NMR spectrum for fraction 5. FIG. 6 is the infra-red spectrum for fraction 5.

EXAMPLE II

Preparation of 1-Methyl-3-(2-Methylpropyl)-2-Oxabicyclo[2.2.2]Octane

Reaction:

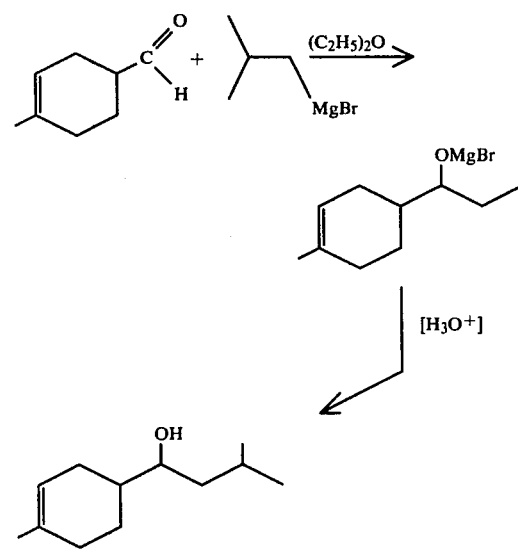

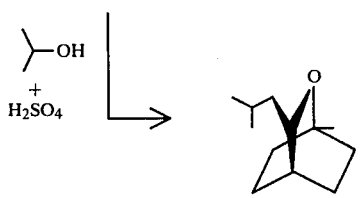

A solution of isobutyl magnesium bromide in ether is prepared by dropwise adding a solution of 517 grams (3.45 moles) of 1-bromo-2-methyl propane in 700 ml of dry ether to a stirred slurry of 76.5 grams of magnesium (3.15 moles) in 600 ml of dry ether under nitrogen at reflux. The resulting solution is stirred at reflux for 30 minutes. A solution of 372 grams of 4-methyl-3-cyclohexenecarboxaldehyde (3.38 moles) in 200 ml of ether is then added to the reaction mixture over a period of one hour at reflux under nitrogen. The resulting slurry is heated at reflux for 30 minutes and then cooled to 0° C. 1200 grams of 20% sulfuric acid is slowly added with external cooling over a 30-minute period. After the addition is complete, two clear layers appear. A distillation head is placed on the flask and ether is distilled from the reaction mixture at atmospheric pressure to a pot temperature of 90° C. 500 ml of water and 300 ml of isopropyl alcohol is added to the reaction mixture. Sulfuric acid (200 grams) is added slowly and the resulting solution is heated to reflux for 9 hours. At the end of this period, the reaction is cooled. 500 ml of water and 200 ml of toluene is added thereto with stirring. The phases are allowed to separate and the aqueous phase is discarded. The organic phase is washed twice with H₂O with sufficient sodium carbonate added to the second wash to adjust to pH to 7-8. Distillation of the organic layer affords 220 grams (1.2 moles) of 1-methyl-3-(2-methylpropyl)-2-oxabicyclo[2.2.2]octane. Fractionation through a 1.5"×12" Goodloe column affords the pure compound (b.p. 62° C., 2.00 mm Hg pressure).

The NMR spectra and IR spectra show fraction 4 of the distillation.

Figure 8:
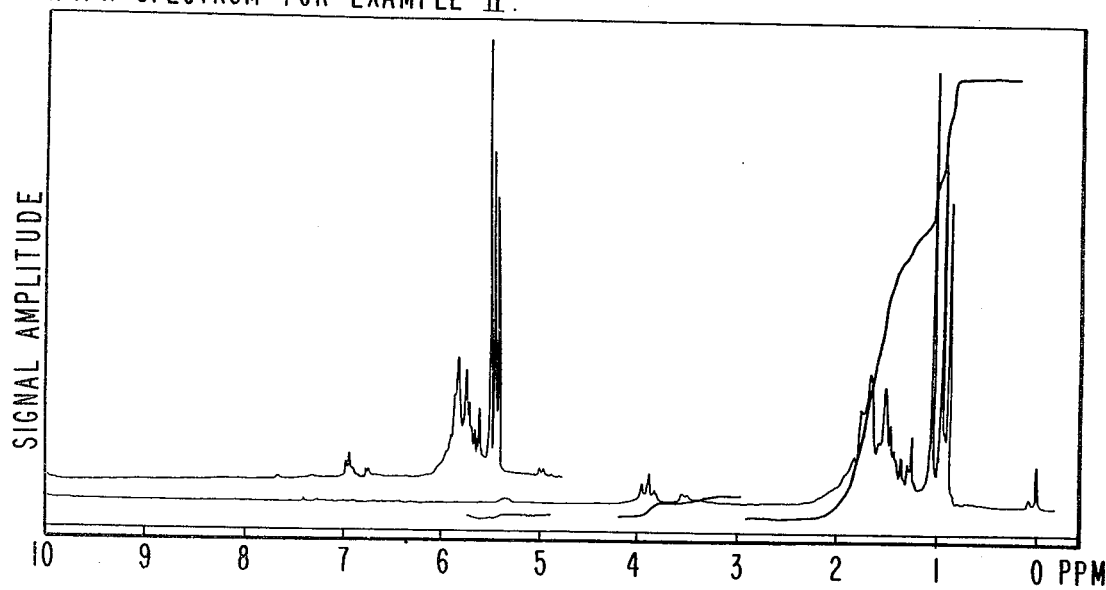
FIG. 8 is the NMR spectrum for fraction 4 of the final product of Example II, the 1-methyl-3-(2-methylpropyl)-2-oxabicyclo[2.2.2]octane.
Figure 9:
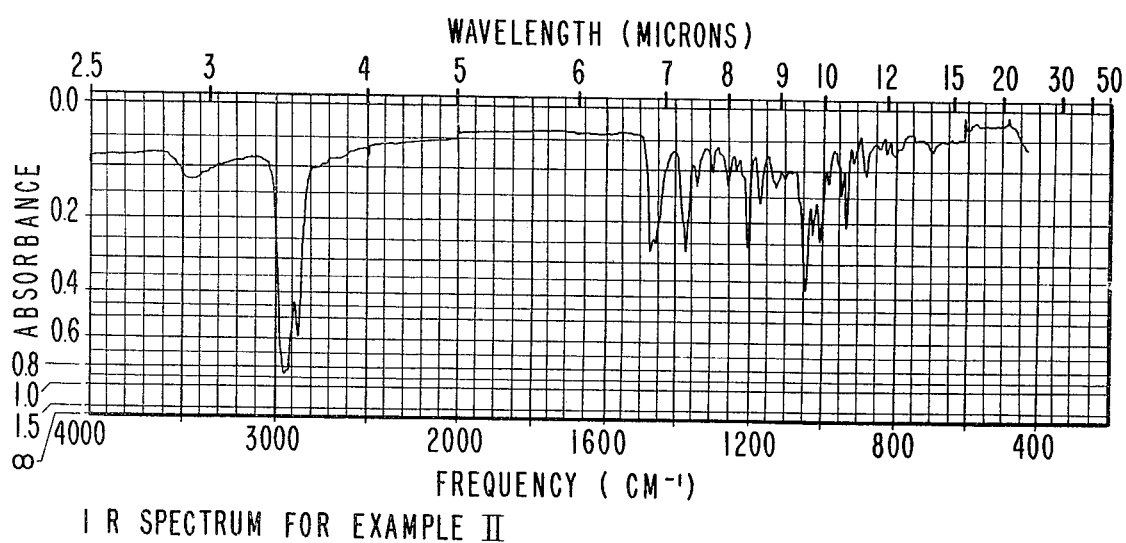
FIG. 9 is the infra-red spectrum for fraction 4 of the oxabicyclooctane produced according to Example II.

The GLC profile for the reaction product is set forth in FIG. 7. The NMR spectrum for fraction 4 is set forth in FIG. 8. The infra-red spectrum for fraction 4 is set forth in FIG. 9.

EXAMPLE III

Preparation of 4,6-Dimethyl-Alpha-Allyl-3-Cyclohexenemethanol

Reaction:

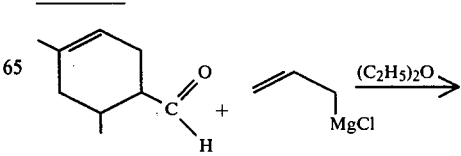

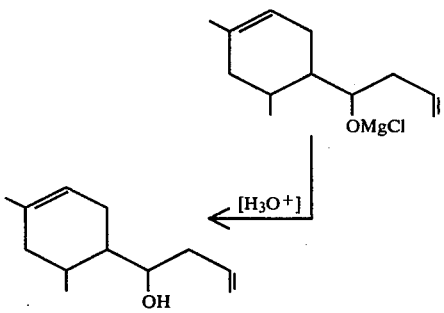

To a stirred slurry of 53 grams of magnesium (2.2 mole) and 500 ml of dry tetrahydrofuran under nitrogen, is added dropwise a solution of 168 grams (2.2 moles) of allyl chloride and 276 grams (2.0 moles) of 4,6-dimethyl-3-cyclohexenecarboxaldehyde at reflux over a two-hour period. The reaction mixture is heated at reflux for 30 minutes, whereupon 400 ml of toluene is added. A distillation head is attached to the reaction flask and the toluene is distilled at atmospheric pressure to a pot temperature of 114° C. The remaining solution is cooled to 0° C., whereupon 900 ml of 18% aqueous hydrochloric acid solution is slowly added with external cooling. Two clear layers are formed. The aqueous layer is discarded and the organic layer is washed twice with water, neutralizing the second wash with caustic soda. The organic layer is quickly distilled. The distillate is fractionally redistilled through a 1"×12" Goodloe packed column to afford 250 grams of 4,6-dimethyl-alpha-allyl-3-cyclohexenemethanol (b.p. 102°, 3.2 mm Hg pressure).

Figure 11:
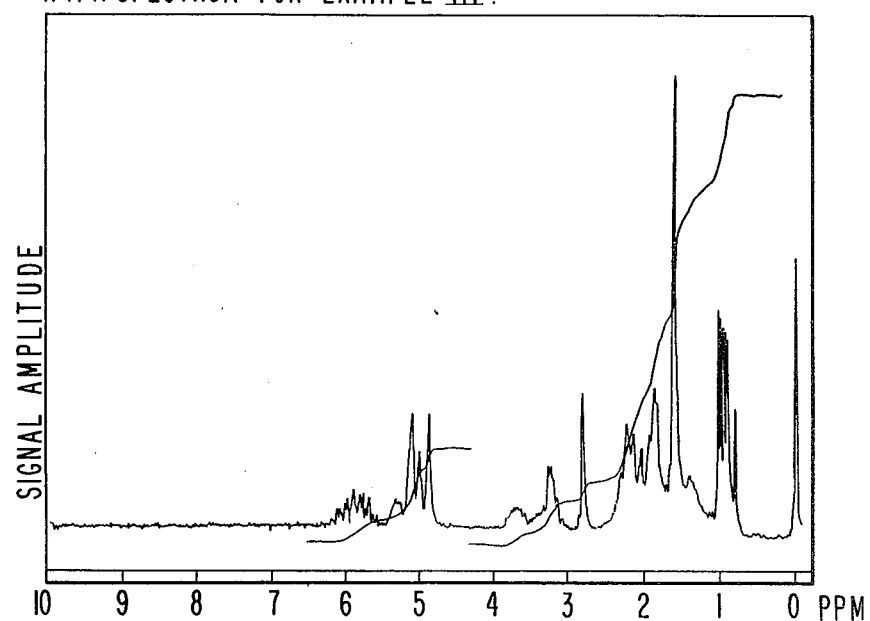
FIG. 11 is the NMR spectrum for the product produced according to Example III.
Figure 12:
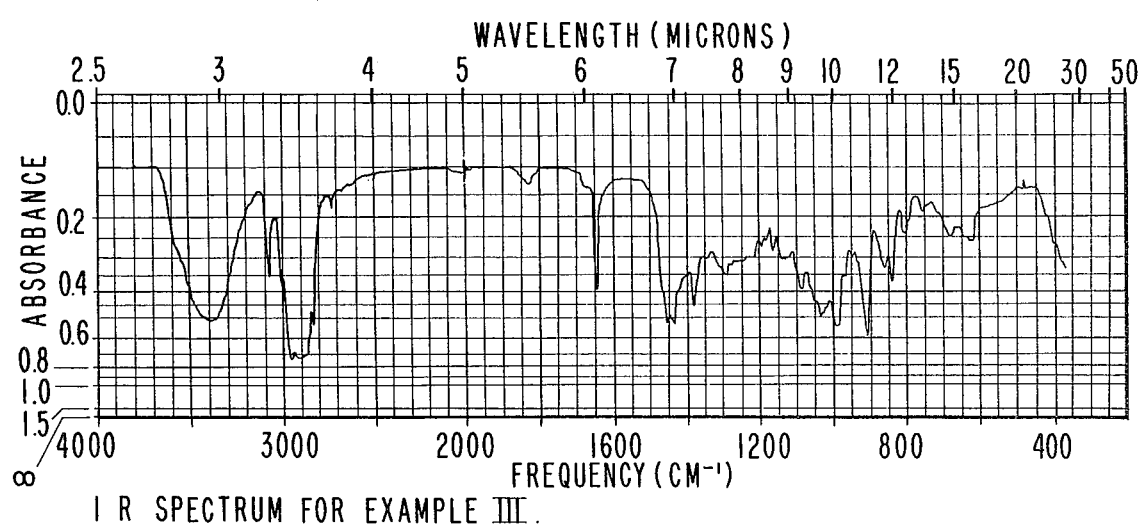
FIG. 12 is the infra-red spectrum for the product produced according to Example III.

The GLC profile for the reaction product produced in this example is set forth in FIG. 10. The NMR spectrum is set forth in FIG. 11. The infra-red spectrum is set forth in FIG. 12.

EXAMPLE IV

Preparation of 2,4-Dimethyl-Alpha-Allyl-3-Cyclohexenemethanol

Reaction:

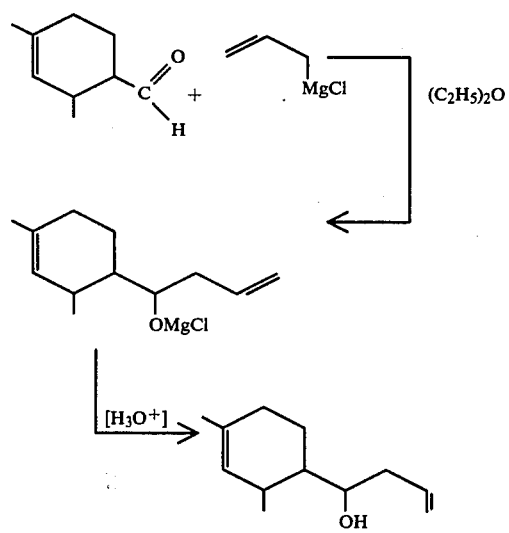

To a stirred slurry of 53 grams of magnesium (2.2 mole) and 500 ml of dry tetrahydrofuran, under nitrogen, is dropwise added a solution of 168 grams (2.2 moles) of allyl chloride and 276 grams (2.0 moles) of 4,6-dimethyl-3-cyclohexenecarboxaldehyde at reflux (67° C.) over a two-hour period. The reaction mixture is heated to reflux for 30 minutes, whereupon 400 ml of toluene is added. A distillation head is attached to the reaction flask and the tetrahydrofuran is distilled off at atmospheric pressure to a pot temperature of 114° C. The remaining solution is cooled to 0° C., whereupon 900 ml of 18% hydrochloric acid solution is slowly added with external cooling. Two clear layers are formed. The aqueous layer is discarded and the organic layer is quickly distilled. The distillate is fractionally redistilled through a 1"×12" Goodloe packed column to afford 250 grams of 4,6-dimethyl-alpha-allyl-3-cyclohexenemethanol (b.p. 88°, 2.0 mm Hg pressure).

Figure 13:
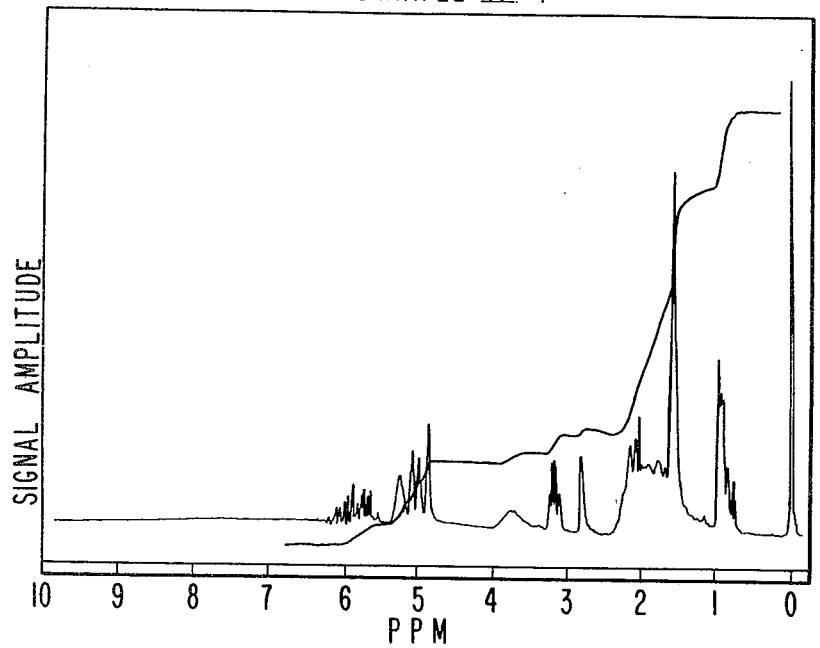
FIG. 13 is the NMR spectrum for the product produced according to Example IV.
Figure 14:
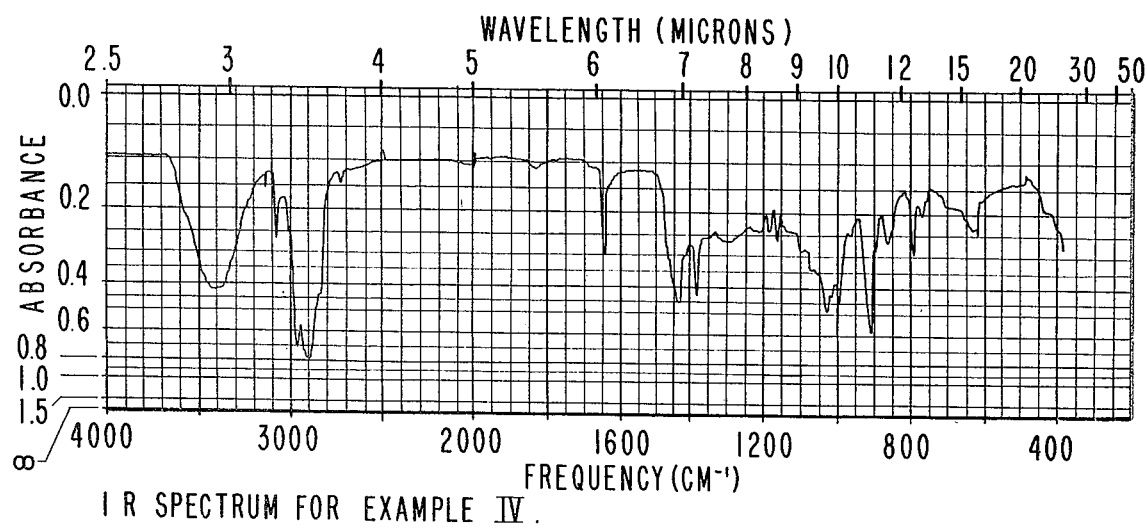
FIG. 14 is the infra-red spectrum for the product produced according to Example IV.

The NMR spectrum is set forth in FIG. 13. The infra-red spectrum is set forth in FIG. 14.

EXAMPLE V

Reaction:

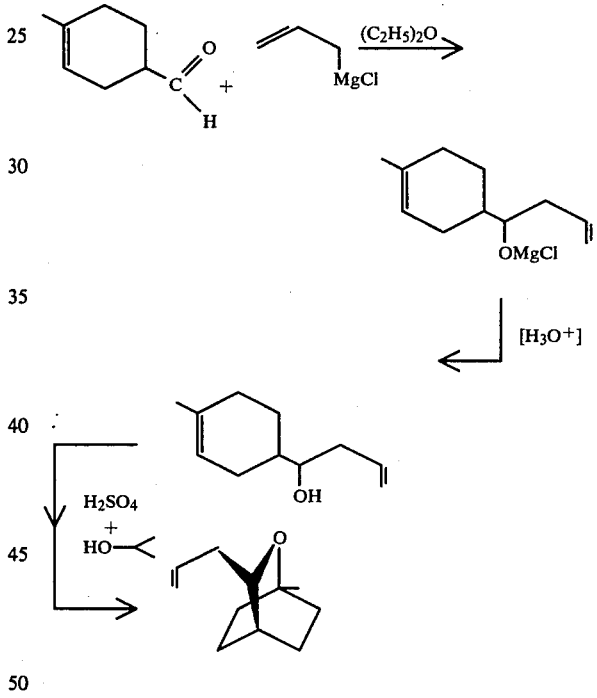

Part V(A): Preparation of Alpha-Allyl-4-Methyl-3-Cyclohexene Methanol

A solution of 251 grams (3.3 moles) of allyl chloride and 372 grams (3 moles) of 4-methyl-3-cyclohexenecarboxaldehyde is added dropwise to a stirred slurry of 77 grams of magnesium (3.2 moles) and 1500 ml of tetrahydrofuran at reflux under nitrogen over a three-hour period. The reaction mixture is heated at reflux (71° C.) for 30 minutes after the feed is complete, whereupon 500 ml of toluene is added. A distillation head is attached to the reaction flask and the tetrahydrofuran is distilled off at atmospheric pressure to a pot temperature of 100° C. The remaining organic solution is cooled to 0° C., whereupon 1000 ml of 18% hydrochloric acid solution is slowly added with external cooling. Two clear layers is formed. The aqueous layer is discarded and the organic layer is quickly distilled. The distillate is fractionally redistilled through a 1.5"×12" Goodloe packed column to afford 325 grams of alpha-allyl-4-methyl-3-cyclohexene methanol (b.p. 92° C., 3.0 mm Hg pressure).

Figure 15:
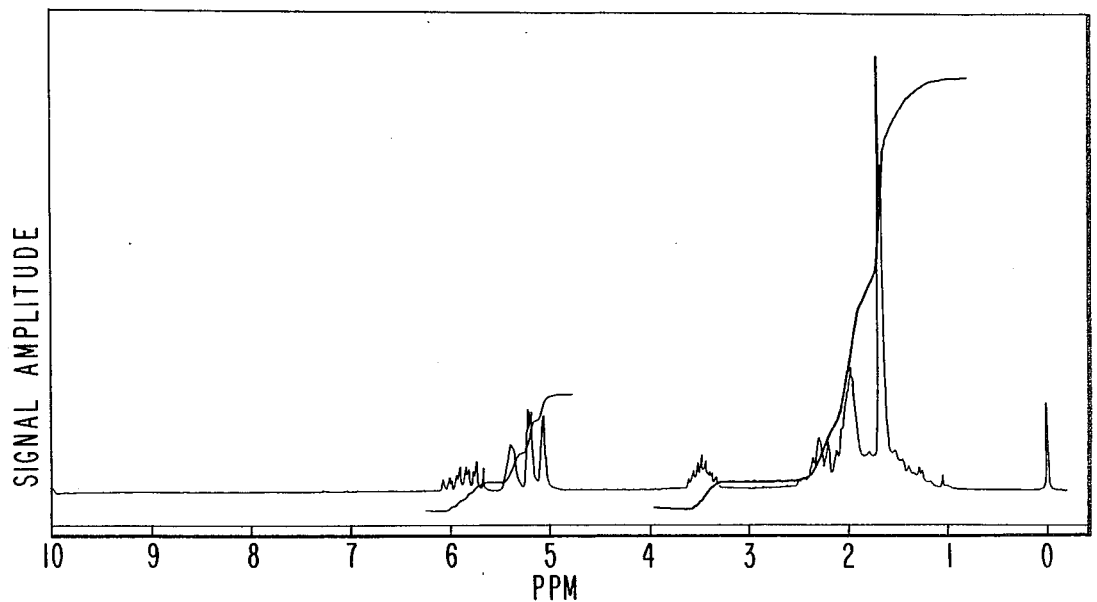
FIG. 15 is the NMR spectrum for the product produced according to Example V(A).
Figure 16:
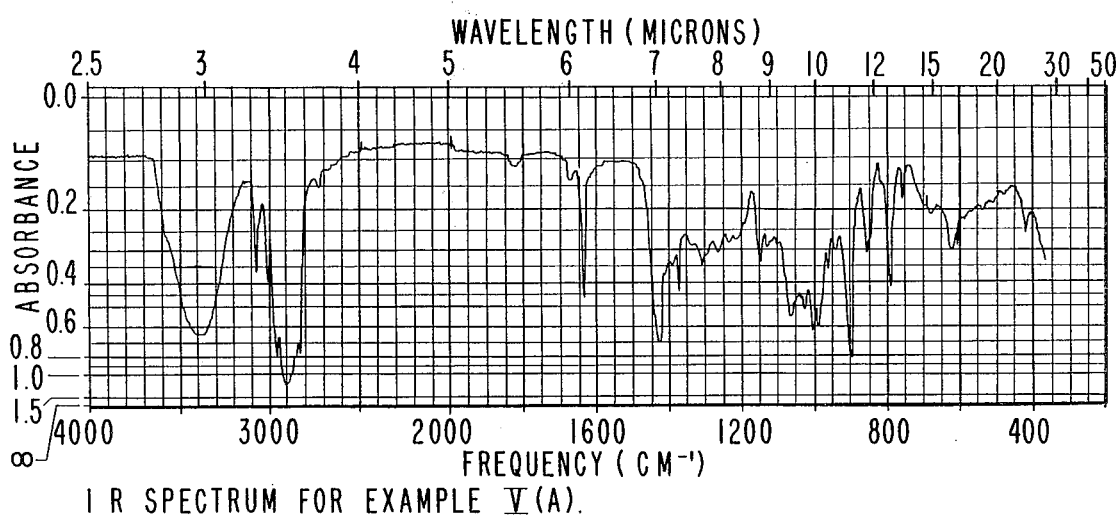
FIG. 16 is the infra-red spectrum for the product produced according to Example V(A).

The NMR spectrum is set forth in FIG. 15. The infra-red spectrum is set forth in FIG. 16.

Part V(B): Preparation of 3-Allyl-1-Methyl-2-Oxabicyclo[2.2.2]Octane

A solution of 848 grams of alpha-allyl-4-methyl-3-cyclohexenyl methanol, 5 liters of water, 750 grams of sulfuric acid and 1000 grams of isopropyl alcohol is heated to reflux for 24 hours. At the end of this period an additional 750 grams of sulfuric acid is added and heating is continued for another 5 hours. At the end of this time, the reaction mass is cooled and 500 ml of toluene is added thereto. The organic layer is washed twice with water and fractionally distilled through a 1.5"×12" Goodloe packed column to afford 692 grams of 3-allyl-1-methyl-2-oxabicyclo[2.2.2]octane (b.p. 68° C., 4 mm Hg pressure).

The NMR spectra and IR spectra consist of fraction 4.

The NMR spectrum for fraction 4 is set forth in FIG. 17. The infra-red spectrum for fraction 4 is set forth in FIG. 18.

EXAMPLE VI

Reaction:

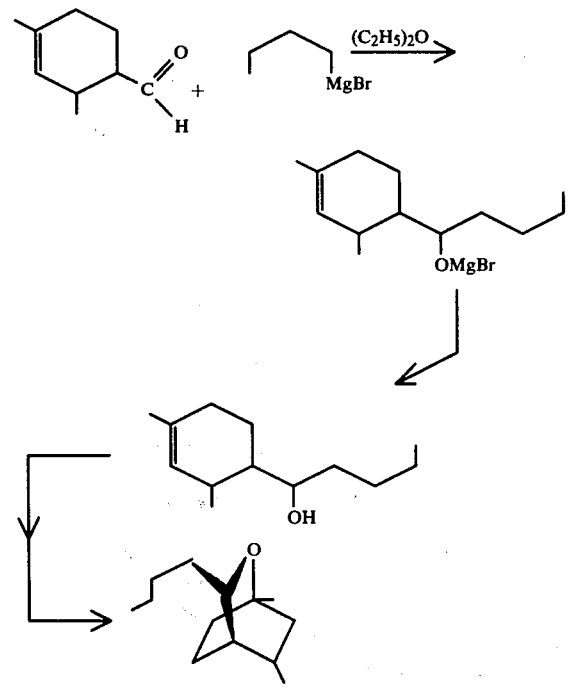

Part VI(A): Preparation of Alpha-n-Butyl-2,4-Dimethyl-3-Cyclohexene Methanol A solution of 782 grams (5.75 moles) of 1-bromobutane is added dropwise over a three-hour period to a stirred slurry of 131 grams (5.4 moles) of magnesium in 1200 ml of dry ether under nitrogen at reflux. The resulting solution is stirred at reflux for ½ hour. A solution of 690 grams (5 moles) of 2,4-dimethyl-3-cyclohexenecarboxaldehyde in 400 ml of ether is added at reflux over a two-hour period. The resulting mixture is stirred at reflux for ½ hour, whereupon it is cooled to 0° C. 1500 ml of 17% hydrochloric acid solution is slowly added with external cooling. Two clear layers is formed. The aqueous layer is discarded and the organic layer is washed twice with water, neutralizing with aqueous caustic soda on the second wash. Distillation through a 2" stone packed column affords 850 grams of a mixture containing alpha-n-butyl-2,4-dimethyl-3-cyclohexene methanol and 3-butyl-1,5-dimethyl-2-oxabicyclo[2.2.2]octane. Fractional distillation through a 1.5"×12" Goodloe packed column affords 346 grams of alpha-n-butyl-2,4-dimethyl-3-cyclohexene methanol (b.p. 113° C., 1.8 mm Hg pressure).

Figure 19:
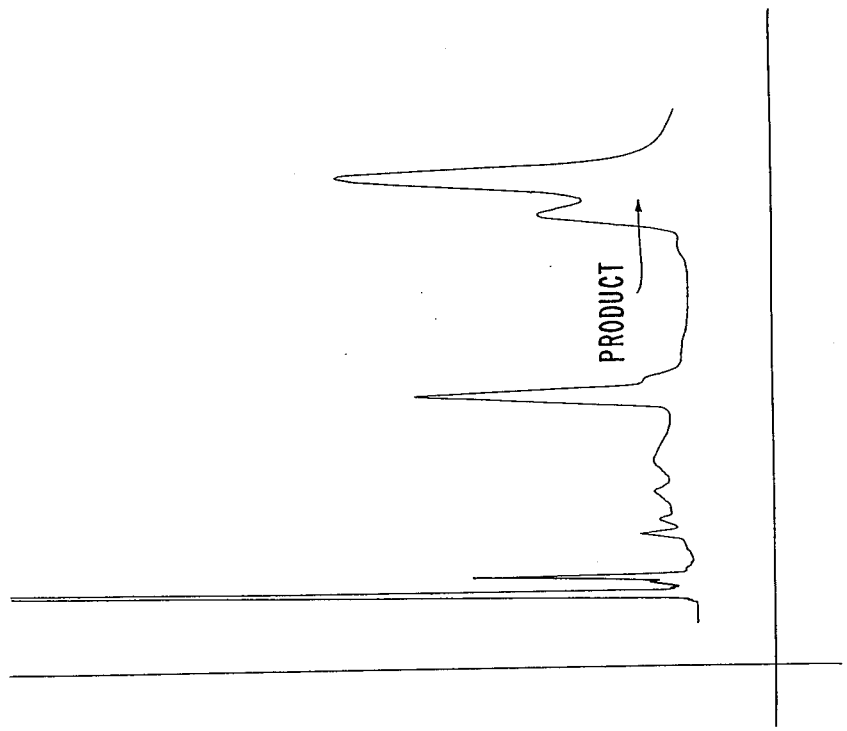
FIG. 19 is the GLC profile for the product produced according to Example VI(A).

The GLC profile for the reaction product is set forth in FIG. 19.

Part VI(B): Preparation of 3-n-Butyl-2,5-Dimethyl-2-Oxabicyclo[2.2.2]Octane

A solution of 746 grams of the reaction product of Example VI(A) in 1800 ml water, 200 grams of sulfuric acid, 400 ml isopropyl alcohol, and 746 grams of an oil consisting of a mixture of alpha-n-butyl-2,4-dimethyl-3-cyclohexene methanol and 3-butyl-2,5-dimethyl-2-oxabicyclo[2.2.2]octane is heated to reflux for 8 hours. At the end of this time, the reaction mixture is cooled and 1 liter of water and 400 ml of toluene is added thereto. The aqueous layer is discarded and the organic layer is washed twice with water, neutralizing the second wash with aqueous caustic soda. Distillation through a 1.5"×12" Goodloe column affords 533 grams of 3-n-butyl-2,5-dimethyl-2-oxabicyclo[2.2.2]octane (b.p. 120° C., 4 mm Hg pressure).

Figure 20:
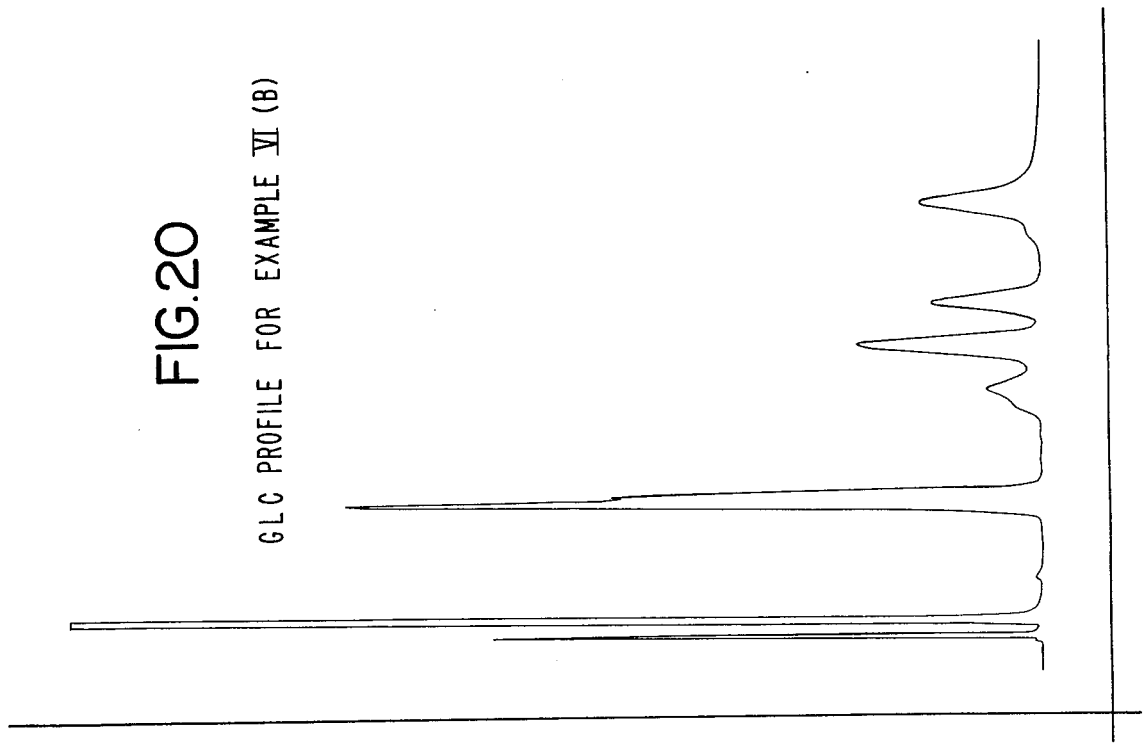
FIG. 20 is the GLC profile for the product produced according to Example VI(B).
Figure 21:
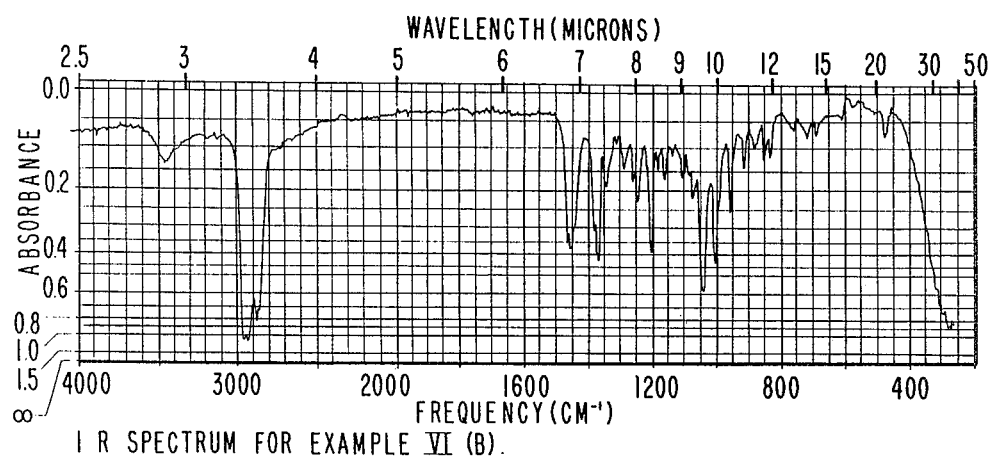
FIG. 21 is the infra-red spectrum for the product produced according to Example VI(B), the 3-butyl-2,5-dimetyl-2-oxabicyclo[2.2.2]octane.

FIG. 20 is the GLC profile of the reaction product thus produced. FIG. 21 is the infra-red spectrum confirming that the substance produced is 3-n-butyl-2,5-dimethyl-2-oxabicyclo[2.2.2]octane.

Reaction:

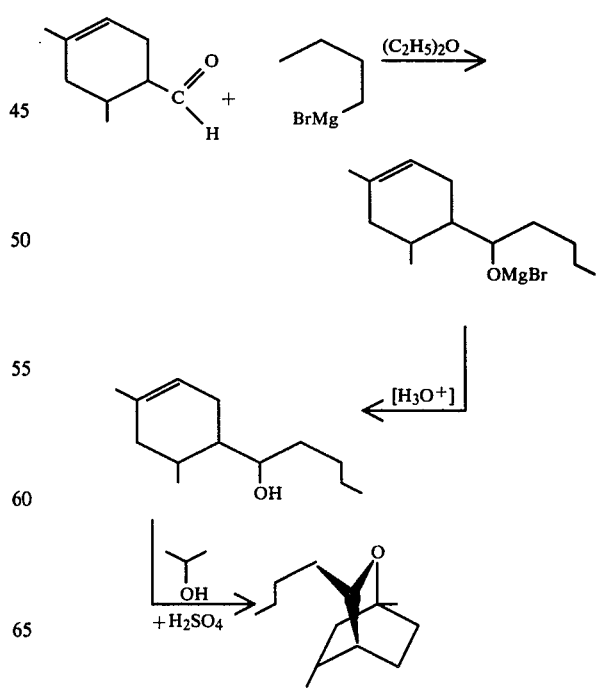

Part VII(A): Preparation of Alpha-n-Butyl-4,6-Dimethyl-3-Cyclohexene Methanol A solution of 469 grams (3.45 moles) of 1-bromobutane in 400 ml of ether is added dropwise under nitrogen to a stirred slurry of 78 grams (3.2 moles) of magnesium in 800 ml of ether under nitrogen. After the addition is complete, the reaction mixture is heated at reflux for 30 minutes. To the boiling mixture is added a solution of 474 grams (3 moles) of 4,6-dimethyl-3-cyclohexenyl-caboxaldehyde in 200 ml of dry ether over a 90 minute period. After the addition, the reaction mixture is heated at reflux for an additional 30 minutes (42° C.). The reaction mass is cooled to 0° C. and 750 ml of 33% aqueous acetic acid is added dropwise with external cooling. Two clear layers are formed. The aqueous layer is discarded and the organic layer is washed twice with water, neutralizing with aqueous bicarbonate on the second wash. Distillation through a 1.5"×12" Goodloe column affords 500 grams of alpha-n-butyl-4,6-dimethyl-3-cyclohexene methanol (b.p. 93° C., 0.8 mm Hg pressure).

Figure 22:
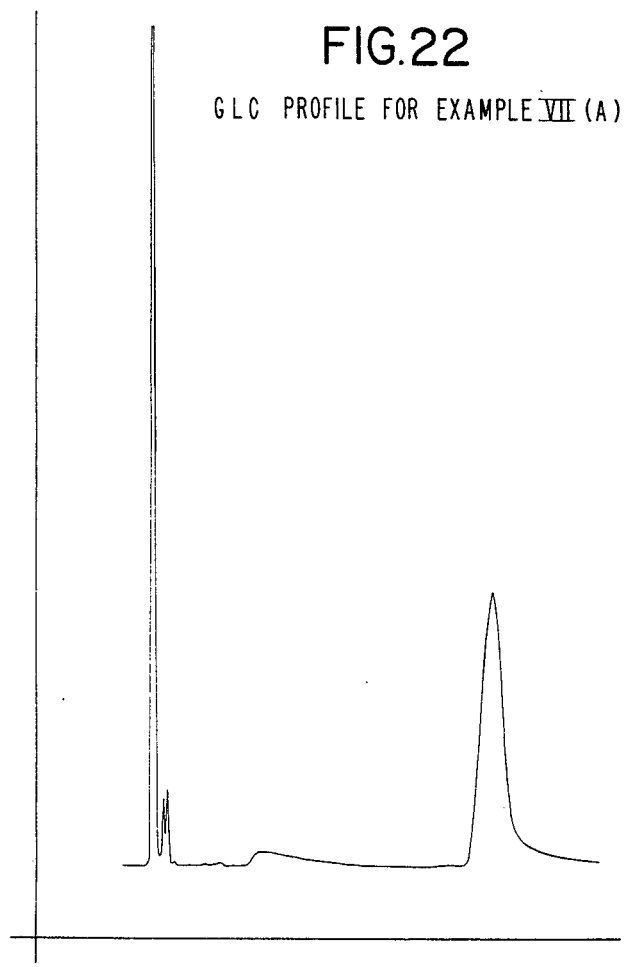
FIG. 22 is the GLC profile for the product produced according to Example VII(A).
Figure 23:
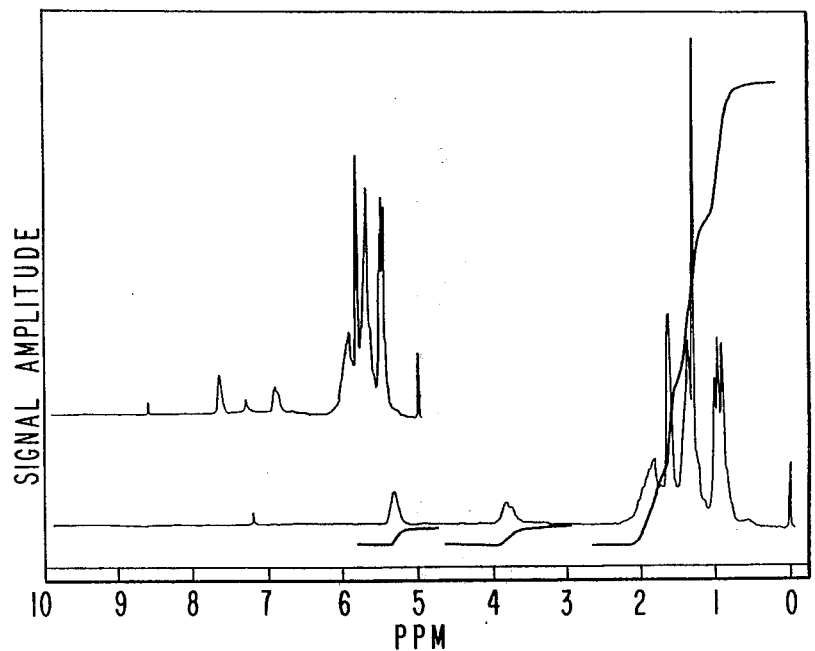
FIG. 23 is the NMR spectrum for the product produced according to Example VII(A).
Figure 24:
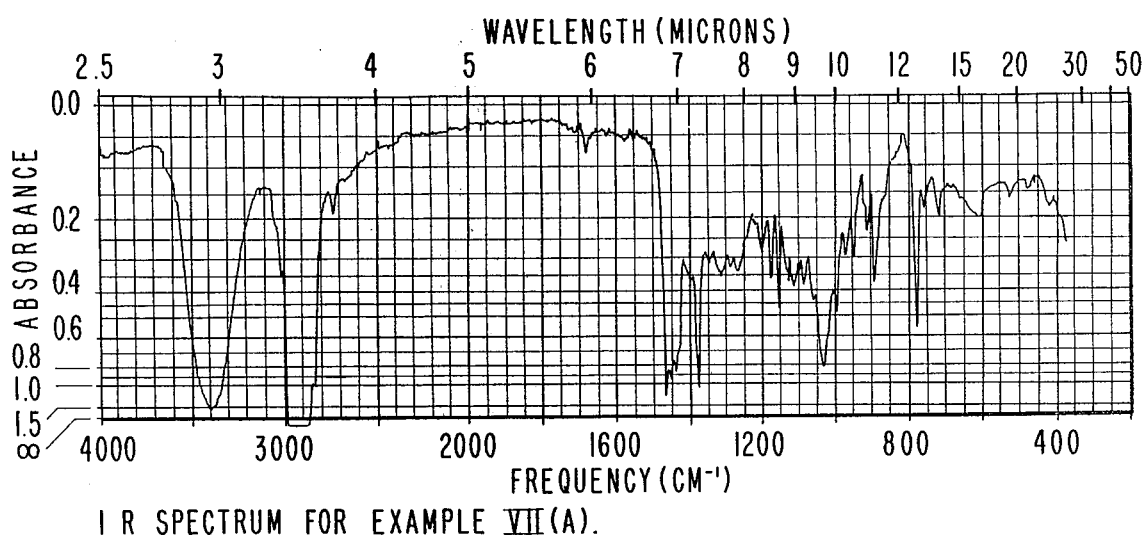
FIG. 24 is the infra-red spectrum for the product produced according to Example VII(A).

The GLC profile for this reaction product is set forth in FIG. 22. The NMR spectrum for alpha-n-butyl-4,6-dimethyl-3-cyclohexene methanol is set forth in FIG. 23. The infra-red spectrum for this compound is set forth in FIG. 24.

Part VII(B): Preparation of 3-n-Butyl-1,5-Dimethyl-2-Oxabicyclo[2.2.2]Octane A solution of 500 grams of alpha-n-butyl-4,6-dimethyl-3-cyclohexene methanol, 600 grams of sulfuric acid, 1400 grams of water and 500 grams of isopropyl alcohol is heated at reflux for 14 hours. The reaction mass is cooled, diluted with 1500 ml of H₂O and 200 ml of toluene. The aqueous layer is discarded and the organic layer is washed twice with water, neutralizing with aqueous sodium hydroxide on the second wash. Distillation through a 1.5"×12" Goodloe column affords 351 grams of 3-n-butyl-1,5-dimethyl-2-oxabicyclo[2.2.2]octane (b.p. 90° C., 3 mm Hg pressure).

Figures 27, 28:
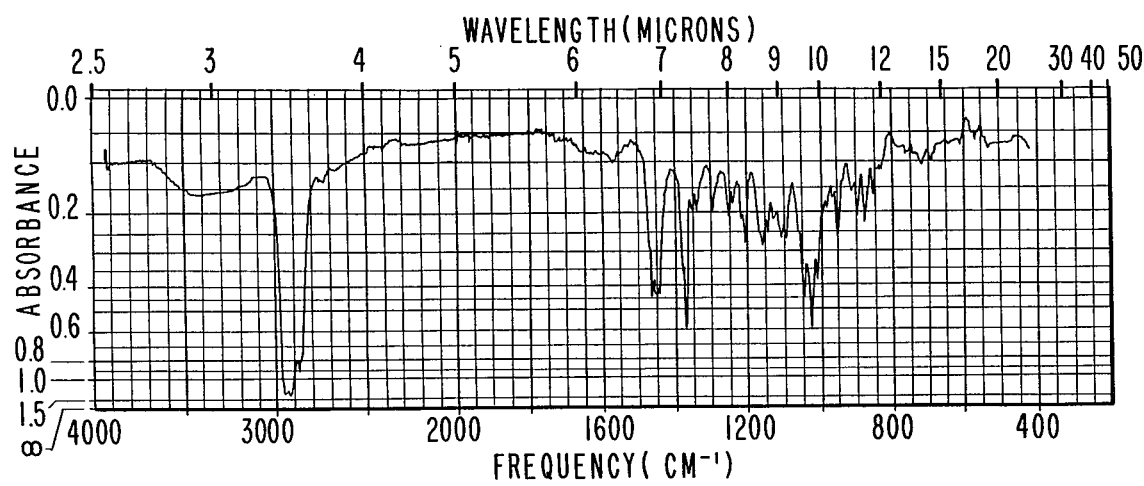
FIG. 27 is the infra-red spectrum for the product produced according to the process of Example VII(B).
FIG. 28 is the GLC profile for the product produced according to Example VIII.

FIG. 25 is the GLC profile for this reaction product at the end of 5 hours of reaction time. FIG. 26 is the NMR spectrum for the resulting reaction product. FIG. 27 is the infra-red spectrum for the resulting product, 3-n-butyl-1,5-dimethyl-2-oxabicyclo[2.2.2]octane.

EXAMPLE VIII

Preparation of 3-Isopropyl-1-Methyl-2-Oxabicyclo[2.2.2]Octane

Reaction:

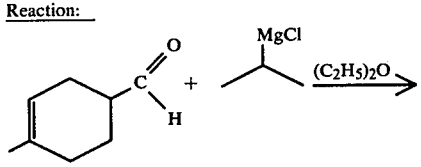

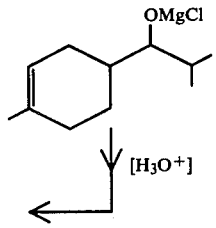

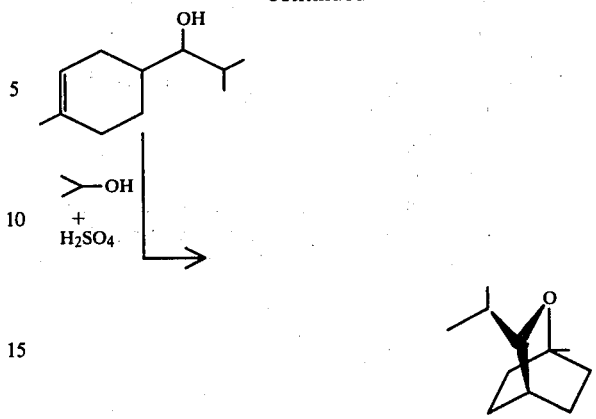

A solution of isopropyl magnesium chloride in ether is prepared by dropwise adding a solution of 410 grams (3.45 moles) of isopropyl chloride in 700 ml of dry ether to a stirred slurry of 76.5 grams of magnesium (3.15 moles) in 600 ml of dry ether under nitrogen at reflux. The resulting solution is stirred at reflux for 30 minutes. A solution of 372 grams of 4-methyl-3-cyclohexenecarboxaldehyde (3.38 moles) in 200 ml of ether is then added to the reaction mixture over a period of 1 hour at reflux under nitrogen. The resulting slurry is heated at reflux for 30 minutes and then cooled to 0° C. 1200 grams of 20% sulfuric acid is slowly added with external cooling over a 30 minute period. After the addition is complete, two clear layers appear. A distillation head is placed on the flask and ether is distilled from the reaction mixture at atmospheric pressure to a pot temperature of 90° C. 500 ml of water and 300 ml of isopropyl alcohol is added to the reaction mixture. Sulfuric acid (200 grams) is added slowly and the resulting solution is heated to reflux for 9 hours. At the end of this period the reaction mass is cooled. 500 ml of water and 200 ml of toluene is added thereto with stirring. The phases are allowed to separate and the aqueous phase is discharged. The organic phase is washed twice with H₂O, with sufficient sodium carbonate added to the second wash to adjust to pH to 7–8. Distillation of the organic layer affords 255 grams of 3-isopropyl-1-methyl-2-oxabicyclo[2.2.2]octane.

The NMR and IR spectra show fraction 10 of the distillation.

FIG. 28 is the GLC profile for the reaction product (Conditions: 180° isothermal; SE-30 column). The NMR spectrum for the resulting reaction product is set forth in FIG. 29. The infra-red spectrum for the resulting reaction product is set forth in FIG. 30.

EXAMPLE IX

Preparation of 1,5-Dimethyl-3-n-Propyl-2-Oxabicyclo[2.2.2]Octane

Reaction:

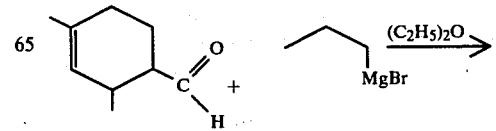

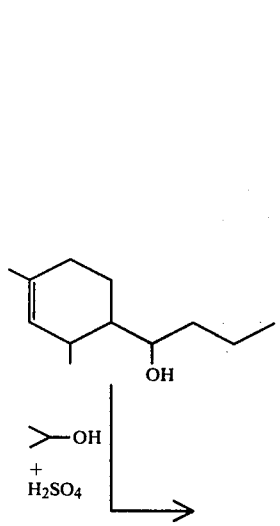
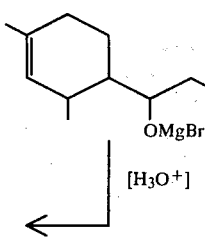

A solution of n-propyl magnesium bromide in ether is prepared by dropwise adding a solution of 469 grams (3.45 moles) of 1-bromopropane in 700 ml of dry ether to a stirred solution of 76.5 grams of magnesium (3.15 moles) in 600 ml of dry ether under nitrogen at reflux. The resulting solution is stirred at reflux for 30 minutes. A solution of 414 grams of 2,4 -dimethyl-3-cyclohexenecarboxaldehyde (3.38 moles) in 200 ml of ether is then added to the reaction mixture over a period of 1 hour at reflux under nitrogen. The resulting slurry is heated at reflux for 30 minutes and then cooled to 0° C. 1200 grams of 20% sulfuric acid is slowly added with external cooling over a 30 minute period. After the addition is complete, two clear layers appear. A distillation head is placed on the flask and ether is distilled from the reaction mixture at atmospheric pressure to a pot temperature of 90° C. 500 ml of water and 300 ml of isopropyl alcohol is added to the reaction mixture. Sulfuric acid (200 grams) is added slowly and the resulting solution is heated to reflux for 9 hours. At the end of this period, the reaction is cooled. 500 ml of water and 200 ml of toluene is added thereto with stirring. The phases are allowed to separate and the aqueous phase is discarded. The organic phase is washed twice with H$_2$O with sufficient sodium carbonate added to the second wash to adjust to pH to 7-8. Distillation of the organic layer affords 288 grams of 2,4-dimethyl-3-n-propyl-2-oxabicyclo[2.2.2]octane.

The NMR and IR spectra represent fraction 10 of the distillation.

Figure 33:
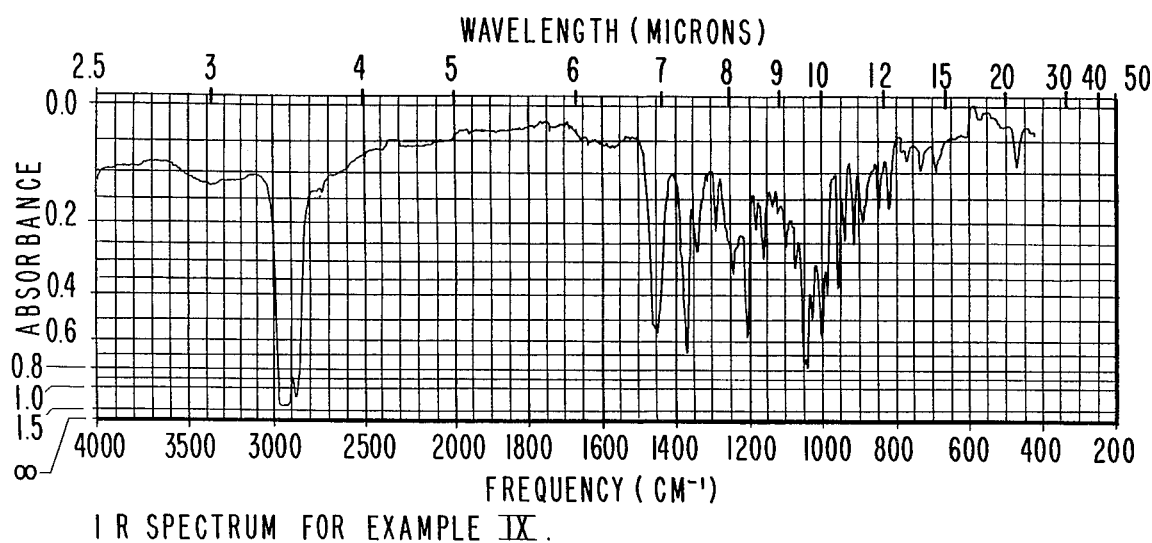
FIG. 33 is the infra-red spectrum for the product produced according to the process of Example IX.

FIG. 31 is the GLC profile for the reaction product of this example. FIG. 32 is the NMR spectrum for the reaction product of this example, 2,4-dimethyl-3-n-propyl-2-oxabicyclo[2.2.2]octane. FIG. 33 is the infra-red spectrum for this reaction product.

EXAMPLE X

Preparation of 1,5-Dimethyl-3-n-Pentyl-2-Oxabicyclo[2.2.2]Octane

Reaction:

A solution of n-pentyl magnesium bromide in ether is prepared by dropwise adding a solution of 521 grams of 1-bromopentane in 700 ml of ether to a stirred slurry of 76.5 grams of magnesium in 600 ml of ether under nitrogen at reflux. The resulting solution is stirred at reflux for 30 minutes under nitrogen. A solution of 414 grams of 2,4-dimethyl-3-cyclohexenylcarboxaldehyde in 200 ml of ether is then added to the reaction mass over a period of 1 hour at reflux under nitrogen. The resulting slurry is heated at reflux for 30 minutes and then cooled to 0° C. 1150 grams of 25% acetic acid is slowly added with external cooling over a 30 minute period. After the addition is complete, two clear layers are obtained. A distillation head is placed on the flask and ether is distilled from the reaction mixture at atmospheric pressure and ether is distilled from the reaction mixture. Sulfuric acid (200 grams) is slowly added and the resulting solution is heated to reflux for 9 hours. At the end of this period, the reaction mass is cooled and 500 ml of water and 200 ml of toluene is added thereto with stirring. Two clear phases are formed. The organic phase is washed twice with water, with sufficient sodium carbonate added to the second wash to adjust to pH 7-8. Distillation of the organic phase through a short column affords 594 grams of a mixture of alpha-n-pentyl-2,4-dimethyl-3-cyclohexenyl methanol, 2,4-dimethyl-3-cyclohexenyl methanol and 1,5-dimethyl-3-n-pentyl-2-oxabicyclo[2.2.2]octane. Fractional distillation afforded 182.5 grams of 1,5-dimethyl-3-n-pentyl-2-oxabicyclo[2.2.2]octane (b.p. 83° C., 1.68 mm Hg pressure).

The NMR and IR spectra are taken from fraction 7 of the distillation.

Figure 34:
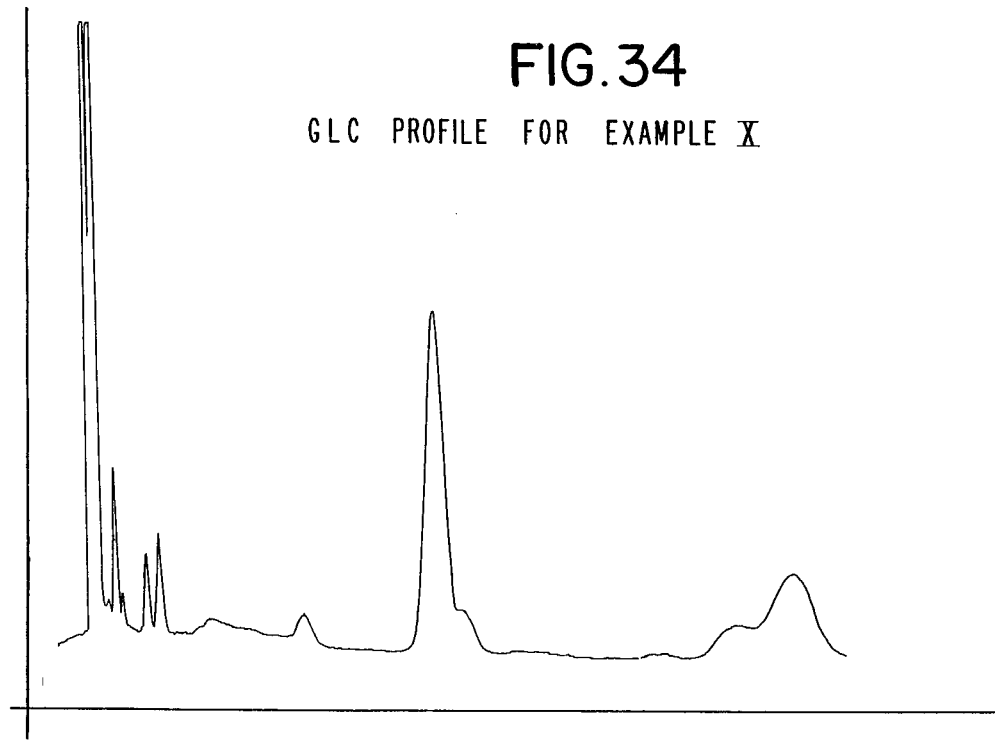
FIG. 34 is the GLC profile for the product produced according to Example X.

FIG. 34 is the GLC profile for the reaction product of this example. FIG. 35 is the NMR spectrum for fraction 7. FIG. 36 is the infra-red spectrum for fraction 7.

EXAMPLE XI

Tomato Juice Formulations

The following tomato juice formulation is prepared by admixing the following ingredients:

| Ingredient | Parts by Weight |
| --- | --- |
| Maltol | 2 |
| Vanillin | 20 |
| Ethyl Vanillin | 3 |
| Anisaldehyde (1% in Propylene Glycol) | 1 |
| Heliotropin (10% in Propylene Glycol) | 2 |
| Ethanol (95%) | 12 |
| Propylene Glycol | 60 |
| TOTAL | 100 |

To a canned tomato juice (manufactured by Campbell Soup Company of Camden, N.J.; ingredients: pure tomato juice, slightly salted) at the rate of 2 ppm are added, one of the following ingredients:
(a) 1-methyl-3-(2-methylpropyl)-2-oxabicyclo[2.2.2]octane prepared according to Example II
(b) 3-n-butyl-2,5-dimethyl-2-oxabicyclo[2.2.2]octane
(c) 1,5-dimethyl-3-n-propyl-2-oxabicyclo[2.2.2]octane produced according to Example IX
(d) 1,5-dimethyl-3-n-pentyl-2-oxabicyclo[2.2.2]octane produced according to Example X Each of the formulations with said 2-oxabicyclo[2.2.2]octane individually added is evaluated by a bench panel of three members. The panel concludes that in each of the cases (a), (b), (c) and (d), the spicey notes are increased with more black pepper notes added both in aroma and taste, and aftertaste in each of cases (a), (b), (c) and (d) being fuller and pleasantly longer lasting.

EXAMPLE XII

Toothpaste Flavor Formulations

The following basic toothpaste flavor formulation is prepared:

| Ingredients | Parts by Weight |
| --- | --- |
| Cardamon Oil | 0.2 |
| Clove Oil | 1.0 |
| Spearmint Oil | 2.0 |
| Peppermint Oil | 96.8 |

This flavor formulation is divided into three portions. Eight parts by weight of the first portion is combined with 2 parts by weight of anethol. Eight parts by weight of the second portion of this flavor is combined with 2 parts by weight of alpha-allyl-4-methyl-3-cyclohexene methanol prepared according to Example V(A). Eight parts by weight of the third portion of this flavor is combined with 2 parts by weight of 2,4-dimethyl-alpha-allyl-3-cyclohexene methanol prepared according to Example IV. Each of the three flavors are compared in water at the rate of 10 ppm and evaluated by a bench panel. Each of the three flavors have sweet anise-like character but the flavor containing the cyclohexene methanol derivatives produced according to Example IV and according to Example V(A) produce, in addition, fuller licorice-related notes and also have additional pleasant nuances; additional sweet, green and fennel notes in the case of use of the product produced according to Example V(A) and additional sweet, floral, fruity, berry-like and green notes in the case of use of the material produced according to Example IV. Therefore, the flavors containing the 2,4-dimethyl-alpha-allyl-3-cyclohexene methanol and also containing the alpha-allyl-4-methyl-3-cyclohexene methanol are each considered by the bench panel as being better and more suitable toothpaste flavors with unique flavor effects.

EXAMPLE XIII

Lemon Flavor Formulation

The following lemon flavor formulation is prepared:

| Ingredients | Parts by Weight |
| --- | --- |
| Natural Lemon Oil, Terpeneless | 10 |
| Acetaldehyde | 0.6 |
| Alpha-terpineol | 2.1 |
| Citral | 1.8 |
| Carvone | 0.24 |
| Terpinolene | 1.2 |
| Alpha-terpinene | 0.25 |
| Diphenyl | 0.25 |
| Alpha Fenchyl Alcohol | 0.25 |
| Limonene | 0.35 |
| Linalool | 0.25 |
| Geranyl Acetate | 0.25 |
| Nootkatone | 0.25 |
| Neryl Acetate | 0.25 |

The flavor formulation is divided into two portions. Four parts per million of 3-isopropyl-1-methyl-2-oxabicyclo[2.2.2]octane prepared according to Example VIII is added to 200 parts per million of the first portion of the lemon flavor prepared above; and to the second portion of the lemon flavor nothing is added. A definite aroma improvement, a more natural lemon juice aroma and taste as well as a pleasant sour effect and generally improved taste with lime nuances is created as a result of the addition of the 3-isopropyl-1-methyl-2-oxabicyclo[2.2.2]octane to the lemon flavor. In general, the 3-isopropyl-1-methyl-2-oxabicyclo[2.2.2]octane supplies a natural "lemon juice" note to this lemon flavor. The flavor is additionally improved still further with addition of 2 parts per million of fenchyl ethyl ether prepared according to application for U.S. Letters Patent, Ser. No. 872,937 filed on Jan. 27, 1978, now U.S. Pat. No. 4,131,687 issued on Dec. 26, 1978.

EXAMPLE XIV

A. Powder Flavor Formulation

20 Grams of the flavor composition of Example XIII is emulsified in a solution containing 300 gm gum acacia and 700 gm water. The emulsion is spray-dried with a Bowen Lab Model Drier utilizing 260 c.f.m. of air with an inlet temperature of 500° F., an outlet temperature of 200° F. and a wheel speed of 50,000 rpm.

B. Sustained Release Flavor

The following mixture is prepared:

| Ingredients | Parts by Weight |
| --- | --- |
| Liquid Lemon Flavor Composition of Example XIII | 20 |
| Propylene glycol | 9 |

| Ingredients | Parts by Weight |
|---|---|
| Cab-O-Sil ® M-5 (Brand of Silica produced by the Cabot Corporation of 125 High Street, Boston, Mass. 02110; Physical Properties: Surface Area: 200 m$^2$gm Nominal particle size: 0.012 microns Density: 2.3 lbs/cu.ft.) | 5.00 |

The Cab-O-Sil is dispersed in the liquid lemon flavor compositions of Example XIII with vigorous stirring, thereby resulting in a viscous liquid. 71 Parts by weight of the powder flavor composition of Part A, supra, is then blended into the said viscous liquid, with stirring, at 25° C. for a period of 30 minutes resulting in a dry, free flowing sustained release flavor powder.

EXAMPLE XV

10 Parts by weight of 50 Bloom pigskin gelatin is added to 90 parts by weight of water at a temperature of 150° F. The mixture is agitated until the gelatin is completely dissolved and the solution is cooled to 120° F. 20 Parts by weight of the liquid flavor composition of Example XIII is added to the solution which is then homogenized to form an emulsion having particle size typically in the range of 2–5 microns. This material is kept at 120° F. under which conditions the gelatin will not jell.

Coacervation is induced by adding slowly and uniformly 40 parts by weight of a 20% aqueous solution of sodium sulphate. During coacervation the gelatin molecules are deposited uniformly about each oil droplet as a nucleus.

Gelation is effected by pouring the heated coacervate mixture into 1,000 parts by weight of 7% aqueous solution of sodium sulphate at 65° F. The resulting jelled coacervate may be filtered and washed with water at temperatures below the melting point of gelatin, to remove the salt.

Hardening of the filtered cake, in this example, is effected by washing with 200 parts by weight of 37% solution of formaldehyde in water. The cake is then washed to remove residual formaldehyde. EXAMPLE XVI

Chewing Gum

100 Parts by weight of chicle are mixed with 4 parts by weight of the flavor prepared in accordance with Example XIV. 300 Parts of sucrose and 100 parts of corn syrup are added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant, long lasting sour lemon flavor.

EXAMPLE XVII

Chewing Gum

100 Parts by weight of chicle are mixed with 18 parts by weight of the flavor prepared in accordance with Example XV. 300 Parts of sucrose and 100 ml of corn syrup are then added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant, long lasting sour lemon flavor.

EXAMPLE XVIII

Toothpaste Formulation

The following separate groups of ingredients are prepared:

| Parts by Weight | Ingredient |
|---|---|
| Group "A" | |
| 30.200 | Glycerine |
| 15.325 | Distilled Water |
| .100 | Sodium Benzoate |
| .125 | Saccharin Sodium |
| .400 | Stannous Fluoride |
| Group "B" | |
| 12.500 | Calcium Carbonate |
| 37.200 | Dicalsium Phosphate (Dihydrate) |
| Group "C" | |
| 2.000 | Sodium N-Lauroyl Sarcosinate (foaming agent) |
| Group "D" | |
| 1.200 | Flavor Material of Example XIV |
| 100.00 - TOTAL | |

Procedure:
1. The ingredients in Group "A" are stirred and heated in a steam jacketed kettle to 160° F.
2. Stirring is continued for an additional three to five minutes to form a homogeneous gel
3. The powders of Group "B" are added to the gel, while mixing, until a homogeneous paste is formed
4. With stirring, the flavor of "D" is added and lastly the sodium-n-lauroyl sarcosinate
5. The resultant slurry is then blended for one hour. The completed paste is then transferred to a three roller mill and then homogenized, and finally tubed.

The resulting toothpaste when used in a normal toothbrushing procedure yields a pleasant lemon flavor, of constant strong intensity throughout said procedure (1–1.5 minutes).

EXAMPLE XIX

Chewable Vitamin Tablets

The flavor material produced according to the process of Example XIV is added to a Chewable Vitamin Tablet. Formulation at a rate of 10 gm/Kg which Chewable Vitamin Tablet formulation is prepared as follows:

In a Hobart Mixer, the following materials are blended to homogeneity:

| | Gms/1000 Tablets |
|---|---|
| Vitamin C (ascorbic acid) as ascorbic acid-sodium ascorbate mixture 1:1 | 70.11 |
| Vitamin B$_1$ (thiamine mononitrate) as Rocoat ® thiamine mononitrate 33⅓% (Hoffman La Roche) | 4.0 |

-continued

| | Gms/1000 Tablets |
|---|---|
| Vitamin B$_2$ (riboflavin) as Rocoat ® riboflavin 33⅓% | 5.0 |
| Vitamin B$_6$ (pyridoxine hydrochloride) as Rocoat ® pyridoxine hydrochloride 33⅓% | 4.0 |
| Niacinamide as Rocoat ® niacinamide 33⅓% | 33.0 |
| Calcium pantothenate | 11.5 |
| Vitamin B$_{12}$ (cyanocobalamin) as Merck 0.1% in gelatin | 3.5 |
| Vitamin E (dl-alpha tocopheryl acetate) as dry Vitamin E acetate 33⅓% | 6.6 |
| d-Biotin | 0.044 |
| Flavor of Example XIV | (as indicated above) |
| Certified lake color | 5.0 |
| Sweetener - sodium saccharin | 1.0 |
| Magnesium stearate lubricant | 10.0 |
| Mannitol q.s. to make | 500.0 |

Preliminary tablets are prepared by slugging with flat-faced punches and grinding the slugs to 14 mesh. 13.5 gm dry Vitamin A Acetate and 0.6 gm Vitamin D are then added as beadlets. The entire blend is then compressed using concave punches at 0.5 gm each.

Chewing of the resultant tablets yields a pleasant, long-lasting, consistently strong lemon flavor with lime nuances for a period of 12 minutes.

EXAMPLE XX

Chewing Tobacco

Onto 100 pounds of tobacco for chewing (85% Wisconsin leaf and 15% Pennsylvania leaf) the following casing is sprayed at a rate of 30%:

| Ingredients | Parts by Weight |
|---|---|
| Corn Syrup | 60 |
| Licorice | 10 |
| Glycerine | 20 |
| Fig Juice | 4.6 |
| Prune Juice | 5 |
| Alpha-allyl-4-methyl-3-cyclohexene methanol prepared according to Example V(A) | 0.04 |

The resultant product is redried to a moisture content of 20%. On chewing, this tobacco has an excellent substantially consistent, long-lasting licorice nuance in conjunction with the tobacco notes.

EXAMPLE XXI

A tobacco is made up by mixing the following materials:

| Ingredient | Parts by Weight |
|---|---|
| Bright | 40.1 |
| Burley | 24.9 |
| Maryland | 1.1 |
| Turkish | 11.6 |
| Stem (flue cured) | 14.2 |
| Glycerine | 2.8 |
| Water | 5.3 |

The above tobacco is used in producing cigarettes, and the following formulation is compounded and incorporated into each of these cigarettes:

| Ingredient | Parts by Weight |
|---|---|
| Ethyl butyrate | .05 |
| Ethyl valerate | .05 |
| Maltol | 2.00 |
| Cocoa extract | 26.00 |
| Coffee extract | 10.00 |
| Ethyl alcohol | 20.00 |
| Water | 41.90 |

The above flavor is incorporated into model "filter" cigarettes at the rate of 0.1%. One-third of these model cigarettes are treated in the tobacco section with 1,5-dimethyl-3-n-pentyl-2-oxabicyclo[2.2.2]octane produced according to Example X at 100 ppm per cigarette. Another one-third of these model cigarettes are treated in the filter with 1,5-dimethyl-3-n-pentyl-2-oxabicyclo[2.2.2]octane produced according to Example X at the rate of 2×10$^{-5}$ gm. When evaluated by paired comparison, the cigarettes treated both in the tobacco and in the filter with the 1,5-dimethyl-3-n-pentyl-2-oxabicyclo[2.2.2]octane are found, in smoke flavor, to be more tobacco-like with enhanced hay, fruity, herbaceous nuances.

EXAMPLE XXII

The following mixture is prepared:

| Ingredients | Parts by Weight |
|---|---|
| Phenylacetic acid | 70.0 |
| Coumarin | 20.0 |
| Phenylethylphenyl acetate | 100.0 |
| Phenyl ethyl alcohol | 5.0 |
| Benzyl benzoate | 100.0 |
| Dimethylphenylethyl carbinol | 10.0 |
| Methyl anthranilate | 5.0 |
| Beta ionone | 10.0 |
| In the alternative, 1,5-dimethyl-3-isopropyl-2-oxabicyclo[2.2.2]octane produced according to Example I(B) or 3-allyl-1-methyl-2-oxabicyclo[2.2.2]octane prepared according to Example V(B) | 30.0 |

The 1,5-dimethyl-3-isopropyl-2-oxabicyclo[2.2.2]octane prepared according to Example I (B) imparts the green, minty, cooling effect to this honey fragrance while also giving it a warm, herbaceous undertone of a rosemary character.

The 3-allyl-1-methyl-2-oxabicyclo[2.2.2]octane prepared according to Example V (B) imparts the minty, eucalyptol-like, buchu-like and caraway-like aroma nuances to this honey formulation while at the same time giving it a warm, herbaceous (garden mint, thyme-like) aroma.

EXAMPLE XXIII

Preparation of a Cosmetic Powder Composition

A cosmetic powder is prepared by mixing in a ball mill, 100 g of talcum powder with 0.25 g of the perfume composition prepared according to Example XXII. It has an excellent minty, green, herbaceous aroma.

EXAMPLE XXIV

Perfumed Liquid Detergent

Concentrated liquid detergents (Lysine salt of n-dodecylbenzene sulfonic acid as more specifically described in U.S. Pat. No. 3,948,818 issued on Apr. 6, 1976) with green, minty, herbaceous aroma nuances are prepared containing 0.10%, 0.15% and 0.20% of the fragrance prepared according to Example XXII. They are prepared by adding and homogeneously mixing the appropriate quantity of fragrance formulation prepared according to Example XXII in the liquid detergent. The detergents all possess excellent green, minty, herbaceous aromas, the intensity increasing with greater concentrations of perfume composition of Example XXII.

EXAMPLE XXV

Preparation of a Cologne and Handkerchief Perfume

The composition prepared according to Example XXII is incorporated into a cologne at concentrations of 2.0%, 2.5%, 3.0%, 3.5%, 4.0%, 4.5%, and 5.0% in 85% aqueous food grade ethanol; and into a handkerchief perfume at concentrations of 15%, 20%, 25%, and 30% (in 95% aqueous food grade ethanol). A distinctive and definite green, herbaceous, minty aroma is imparted to the cologne and to the handkerchief perfume at all levels indicated above.

EXAMPLE XXVI

Preparation of Soap Composition

One hundred grams of soap chips are mixed with one gram of each of the formulations of Example XXII until homogeneous compositions are obtained. In each of the cases, the homogeneous compositions are heated under three atmospheres pressure at 180° C. for a period of three hours and the resulting liquids are placed into soap molds. The resulting soap cakes, on cooling, manifest green, minty, herbaceous aroma.

EXAMPLE XXVII

Preparation of a Solid Detergent Composition

A detergent is prepared from the following ingredients according to Example I of Canadian Pat. No. 1,007,948:

|  | Percent by Weight |
|---|---|
| "Neodol 45-11" (a $C_{14}$—$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is a "phosphate-free" detergent. A total of 100 grams of this detergent is admixed with 0.15 grams of each of the honey base perfumes of Example XXII. Each of the detergent samples has an excellent green, minty, herbaceous aroma, the minty and herbaceous aromas being imparted by the oxybicyclo[2.2.2]octanes prepared according to Examples I and V (B).

EXAMPLE XXVIII

Preparation of a Cosmetic Powder Composition

A cosmetic powder is prepared by admixing in a ball mill, 100 g of talcum powder with 0.25 g of 3-allyl-1-methyl-2-oxabicyclo[2.2.2]-octane prepared according to Example V (B) and 0.25 g of 1,5-dimethyl-3-isopropyl-2-oxabicyclo[2.2.2]octane prepared according to Example I (B). The resulting cosmetic powder has an excellent green, minty, herbaceous, buchu-like, caraway-like aroma with a cooling effect and garden mint, thyme and rosemary nuances.

EXAMPLE XXIX

Perfumed Liquid Detergent

Concentrated liquid detergents (Lysine salt of n-dodecylbenzene sulfonic acid as more specifically described in U.S. Pat. No. 3,948,818 issued on Apr. 6, 1976) with green, minty, herbaceous, eucalpytol-like, buchu-like and caraway aroma notes and rosemary, garden mint, and thyme undertones and having a cooling effect are prepared containing 0.10%, 0.15%, 0.20%, and 0.25% of a 50-50 mixture of 1,5-dimethyl-3-isopropyl-2-oxabicyclo[2.2.2]octane prepared according to Example I (B) and 3-allyl-1-methyl-2-oxabicyclo[2.2.2]-octane prepared according to Example V (B). They are prepared by adding and homogeneously mixing the appropriate quantity of the mixture of 1,5-dimethyl-3-isopropyl-2-oxabicyclo[2.2.2]octane and 3-allyl-1-methyl-2-oxabicyclo[2.2.2]octane in the liquid detergent. The detergents all possess green, minty, herbaceous, eucalyptol-like, bucch-like and caraway-like aroma nuances with rosemary, garden mint and thyme undertone and a cooling effect, the intensity of each of the foregoing characteristics increasing with greater concentrations of 50-50 mixture of 1,5-dimethyl-3-isopropyl-2-oxabicyclo[2.2.2]octane and 3-allyl-1-methyl-2-oxabicyclo[2.2.2]octane.

EXAMPLE XXX

Preparation of Colognes and Handkerchief Perfumes

3-Allyl-1-methyl-2-oxabicyclo[2.2.2]octane prepared according to Example V (B) is incorporated into colognes at concentrations of 2.0%, 2.5%, 3.0%, 3.5%, 4.0% and 4.5% in 85% aqueous food grade ethanol; and into handkerchief perfumes at concentrations of 15%, 20%, 25% and 30% (in 95% aqueous ethanol). Distinctive minty, eucalyptol-like, herbaceous, buchu-like and caraway aroma nuances with garden mint and thyme undertones are imparted to the colognes and to the handkerchief perfumes at the various above levels indicated.

EXAMPLE XXXI

Preparation of Colognes and Handkerchief Perfumes 1,5-Dimethyl-3-isopropyl-2-oxabicyclo[2.2.2]octane prepared according to Example I (B) is incorporated into colognes at concentrations of 2.0%, 2.5%, 3.0%, 3.5%, 4.0% and 4.5% in 90% aqueous food grade ethanol; and into handkerchief perfumes at concentrations of 15%, 20%, 25% (in 95% aqueous food grade ethanol). Distinctive and definitive green, minty, herbaceous aroma nuances with a rosemary type undertone and a cooling effect are imparted to the colognes and to the handkerchief perfumes at the above-indicated levels.

EXAMPLE XXXII

Preparation of α-Allyl-4,6-Dimethyl-3-Cyclohexenylmethyl Acetate

Reaction:

-continued

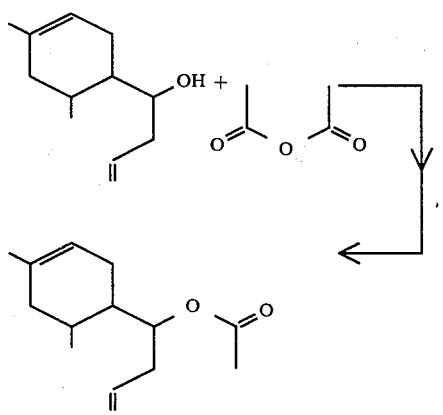

A solution of 101 grams (0.56 moles) of α-allyl-4,6-dimethyl-3-cyclohexenylmethanol and 102 grams of acetic anhydride are heated at reflux (135° C.) for two hours. The reaction mass is cooled to 50° C. and 700 ml of water and 100 ml of toluene are added thereto. The mass is stirred for one hour. The aqueous layer is discarded and the organic layer is washed with water and dilute aqueous sodium bicarbonate respectively. Distillation through a 48" Vigreux column affords 91 grams of α-allyl-4,6-dimethyl-3-cyclohexenylmethyl acetate (boiling point 107° C., mm Hg).

FIG. 37 sets forth the NMR spectrum for fraction 4 resulting from this distillation. FIG. 38 sets forth the infra-red spectrum for fraction 4 resulting from this distillation.

EXAMPLE XXXIII

Preparation of
α-Allyl-2,4-Dimethyl-3-Cyclohexenylmethyl Acetate

Reaction:

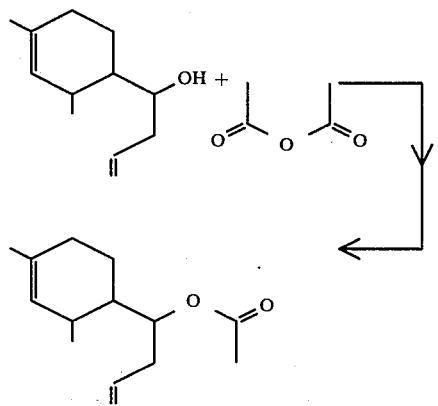

A solution of 156 grams of α-allyl-2,4-dimethyl-3-cyclohexenylmethanol and 172 grams of acetic acid are heated at reflux for a period of two hours. The reaction mass is then cooled to 50° C. and 2 liters of water and 100 ml of toluene are added thereto. The reaction mass is stirred for a period of one hour. The aqueous layer is discarded and the organic layer is washed with water and dilute aqueous sodium carbonate respectively. Distillation through a 1"×12" Vigreux column affords 162 grams of α-allyl-2,4-dimethyl-3-cyclohexenylmethyl acetate (boiling point 84° C., 0.8 mm Hg).

Figure 39:
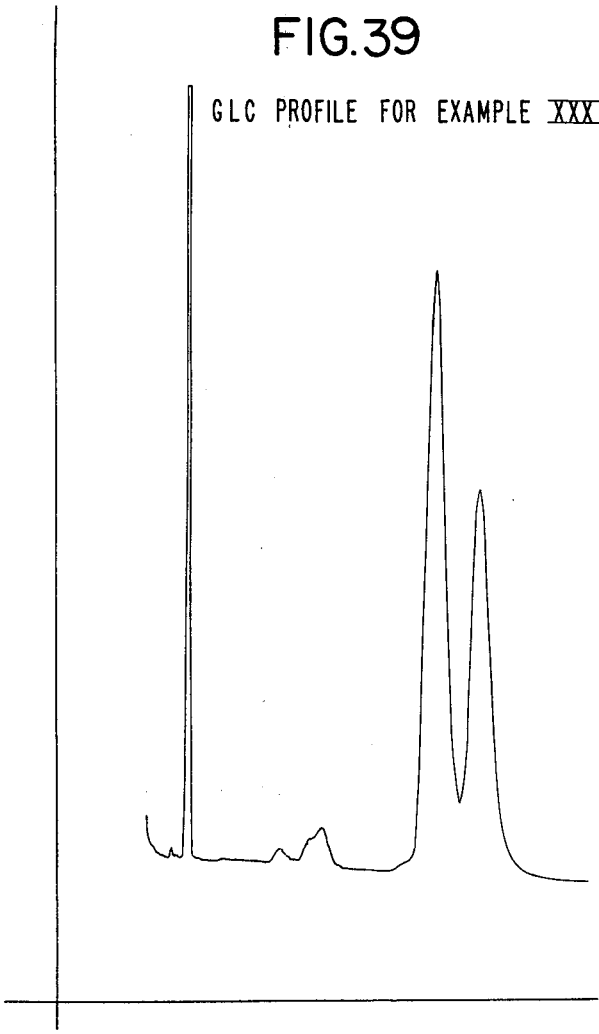
FIG. 39 is the GLC profile for the reaction product produced according to Example XXXIII.

FIG. 39 sets forth the GLC profile for the crude reaction mass (Conditions: 180° C. isothermal, 10% SE-30 column).

Figure 40:
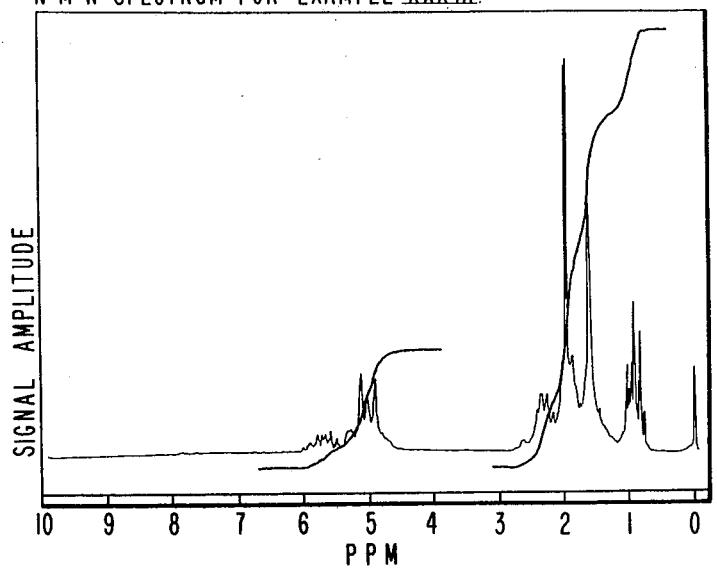
FIG. 40 is the NMR spectrum for the reaction product produced according to Example XXXIII.
Figure 41:
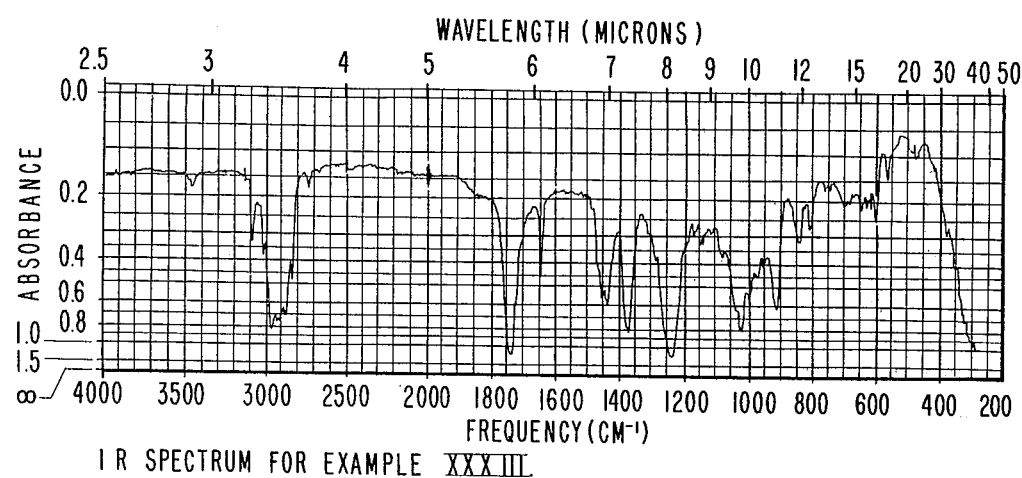
FIG. 41 is the infra-red spectrum for the reaction product produced according to Example XXXIII.

FIG. 40 sets forth the NMR spectrum for the reaction product produced according to this example. FIG. 41 sets forth the infra-red spectrum for the reaction product produced according to this example.

EXAMPLE XXXIV

Preparation of
α-Allyl-4-Methyl-3-Cyclohexenylmethyl Acetate

Reaction:

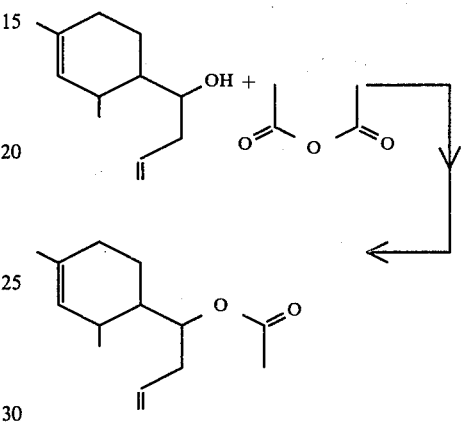

A solution of 195 grams (1.2 moles) of α-allyl-4-methyl-3-cyclohexenylmethanol and 200 grams of acetic anhydride are heated to reflux (138° C.) for 2.5 hours. The reaction mass is cooled to 50° C. and two liters of water and 200 ml of toluene are added thereto. The reaction mass is stirred for a period of 30 minutes. The aqueous layer is discarded and the organic layer is washed successively with 1 liter of water and 1 liter of dilute aqueous sodium bicarbonate. The reaction mass is then stripped of toluene affording 229 grams of an oil. This oil is distilled through a 1"×12" Goodloe packed column to afford 194 grams of α-allyl-4-methyl-3-cyclohexenylmethyl acetate (boiling point 99° C., 3 mm Hg).

Figure 43:
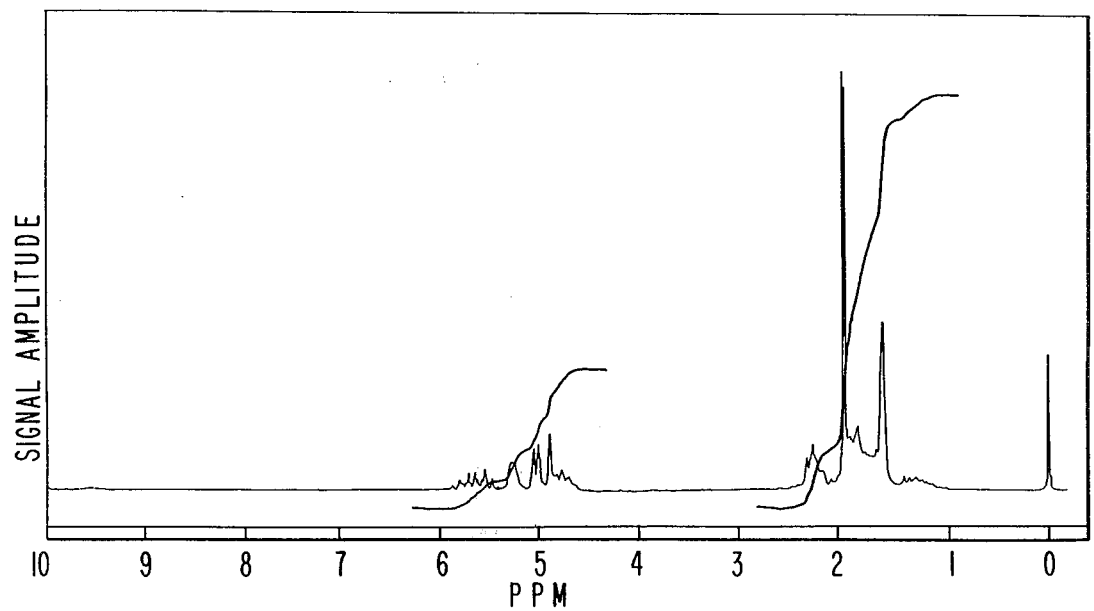
FIG. 43 is the NMR spectrum for fraction 6 of the reaction product produced according to Example XXXIV.

The NMR spectrum for fraction 6 resulting from the above distillation is set forth in FIG. 43.

Figure 44:
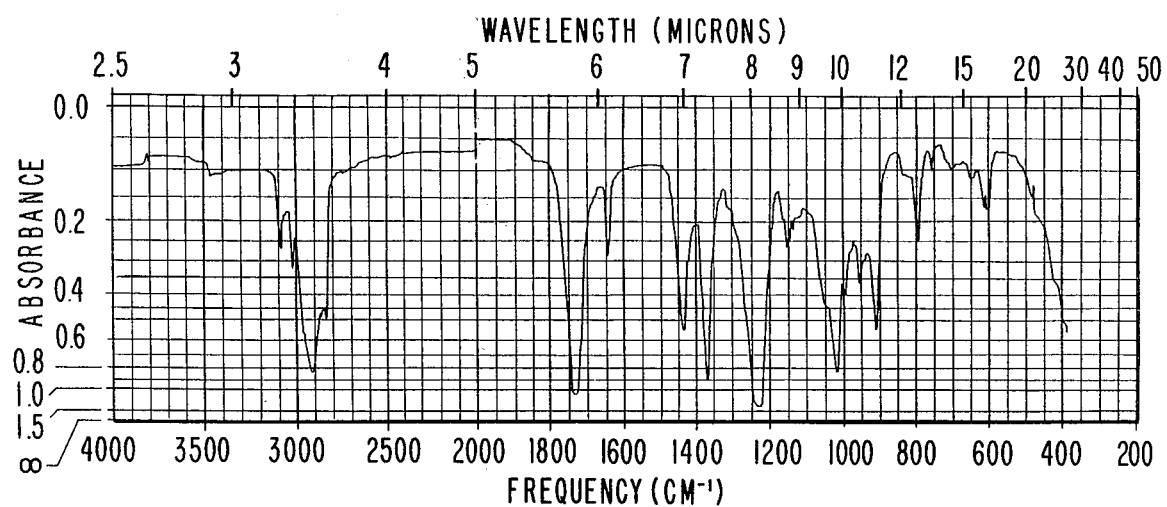
FIG. 44 is the infra-red spectrum for fraction 6 produced according to Example XXXIV.

The infra-red spectrum for fraction 6 resulting from the above distillation is set forth in FIG. 44.

Figure 42:
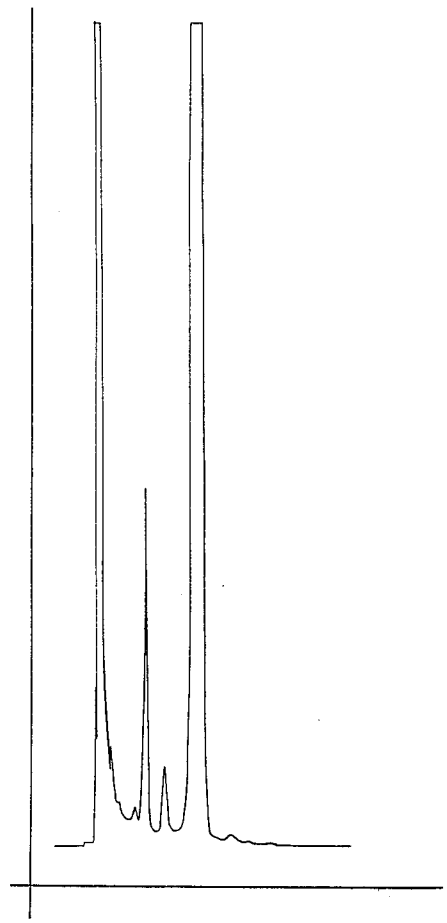
FIG. 42 is the GLC profile for the crude reaction product produced according to Example XXXIV.

FIG. 42 sets forth the GLC profile for the crude reaction product (Conditions: 200° C. isothermal, 10% SE-30 packed column).

EXAMPLE XXXV

Utilizing the procedure of Example I of column 15 of U.S. Pat. No. 3,632,396, a nonwoven cloth substrate useful as a dryer-added fabric-softening article of manufacture is prepared wherein the substrate, the substrate coating and the outer coating and the perfuming material are as follows:

1. a water "dissolvable" paper ("Dissolvo Paper");
2. Adogen 448 (m.p. about 140° F.) as the substrate coating; and
3. an outer coating having the following formulation (m.p. about 150° F.):
   57 percent $C_{20-22}$ HAPS
   22 percent isopropyl alcohol
   20 percent antistatic agent 1 percent of the oxabicyclooctane derivative or cyclohexyl alkyl or alkenyl carbinol or ester thereof of our invention as set forth in the Table I below and giving rise to the aroma nuances as set forth in said Table I below:

TABLE I

| NAME OF COMPOUND | FRAGRANCE CHARACTERISTICS |
|---|---|
| 1,5-Dimethyl-3-isopropyl-2-oxabicyclo[2.2.2]octane | A green, minty, herbaceous (rosemary) aroma with a cooling effect. |
| 3-allyl-1-methyl-2-oxabicyclo[2.2.2]octane | A minty, eucalyptol-like, herbaceous (garden mint, thyme), buchu-like aroma with caraway-like nuances. |
| 3-n-butyl-2,5-dimethyl-2-oxabicyclo[2.2.2]octane | A green, spicey, carvone-like aroma. |
| 1,5-dimethyl-3-n-propyl-2-oxabicyclo[2.2.2]octane | A herbaceous, minty (garden mint) aroma with basil, thyme and caraway nuances. |
| 1,5-dimethyl-3-n-pentyl-2-oxabicyclo[2.2.2]octane | An oily, green, herbaceous (wet lettuce) aroma. |
| α-allyl-4-methyl-3-cyclohexenemethanol | A sweet, anise, carvone-like and minty aroma. |
| 2,4-dimethyl-α-allyl-3-cyclohexenemethanol | A sweet, anisic, citrus aroma with minty, peppery, and geranium-like undertones. |
| α-allyl-4-methyl-3-cyclohexene-1-methanol acetate | A sweet, fruity, herbaceous, floral aroma with carvone-like and geranyl acetate-like nuances. |
| 4,6-dimethyl-α-allyl-3-cyclohexenemethanol | A sweet, herbaceous, fruity aroma with basil and blueberry-like undertones. |
| α-allyl-4,6-dimethyl-3-cyclohexene-1-methanol acetate | A green, fruity, anisic, woody aroma. |
|  | A green, floral, minty, lemonly aroma. |

Fabric-softening compositions prepared as set forth above having the above aroma characteristics essentially consist of a substrate having a weight of about 3 grams per 100 square inches, a substrate coating of about 1.85 grams per 100 square inches of substrate and an outer coating of about 1.4 grams per 100 square inches of substrate, thereby providing a total aromatized substrate and outer coating weight ratio of about 1:1 by weight of the substrate. The aromas as set forth in Table I above are imparted in a pleasant manner to the head space in the dryer on operation thereof using the said dryer added fabric softening nonwoven fabric.

EXAMPLE XXXVI

A liquid detergent composition is prepared according to Example IV of United Kingdom Pat. No. 1,498,520 whereby the following ingredients are admixed:

| Ingredient | Weight % |
|---|---|
| Coconut alcohol ethoxylate | 30% |
| Linear alkyl benzene sulfonate, triethanolamine salt (alkyl = $C_{11.8}$ avg.) | 10% |
| Potassium chloride | 3% |
| Triethanolamine | 3% |
| Triethanolammonium citrate | 2% |
| Ethyl alcohol | 5% |
| Soil release ether "D" | 1.0% |
| Oxabicyclooctane derivative or cyclohexene alkyl or alkenyl carbinol and ester thereof of our invention as set forth in TABLE II | 3.0% |
| Water | Balance |

The soil release ether "D" is defined according to Table II on page 15 of United Kingdom Pat. No. 1,498,520.

This composition is prepared by admixing all of the ingredients exclusive of soil release ether "D" and agitating the mixture until all electrolytes are dissolved. Soil release ether "D" is then admixed with the solution in the form of a dry powder which passes through 150 mesh standard sieve. The resulting composition is in the liquid state and easily pourable. The composition is found not to redden on contact with plastic bottles, does not gel when diluted with water and has a long-lasting aroma composition as defined in the following Table II when the following oxabicyclooctane derivatives or cyclohexene alkyl or alkenyl carbinols or esters thereof are added thereto:

TABLE I

| NAME OF COMPOUND | FRAGRANCE CHARACTERISTICS |
|---|---|
| 1,5-Dimethyl-3-isopropyl-2-oxabicyclo[2.2.2]octane | A green, minty, herbaceous (rosemary) aroma with a cooling effect. |
| 3-allyl-1-methyl-2-oxabicyclo[2.2.2]octane | A minty, eucalyptol-like, herbaceous (garden mint, thyme), buchu-like aroma with caraway-like nuances. |
| 3-n-butyl-2,5-dimethyl-2-oxabicyclo[2.2.2]octane | A green, spicey, carvone-like aroma. |
| 1,5-dimethyl-3-n-propyl-2-oxabicyclo[2.2.2]octane | A herbaceous, minty (garden mint) aroma with basil, thyme and caraway nuances. |
| 1,5-dimethyl-3-n-pentyl-2-oxabicyclo[2.2.2]octane | An oily, green, herbaceous (wet lettuce) aroma. |
| α-allyl-4-methyl-3-cyclohexenemethanol | A sweet, anise, carvone-like and minty aroma. |
| 2,4-dimethyl-α-allyl-3-cyclohexenemethanol | A sweet, anisic, citrus aroma with minty, peppery, and geranium-like undertones. |
| α-allyl-4-methyl-3-cyclohexene-1-methanol acetate | A sweet, fruity, herbaceous, floral aroma with carvone-like and geranyl acetate-like nuances. |
| 4,6-dimethyl-α-allyl-3-cyclohexenemethanol | A sweet, herbaceous, fruity aroma with basil and blueberry-like undertones. |
| α-allyl-4,6-dimethyl-3-cyclohexene-1-methanol acetate | A green, fruity, anisic, woody aroma. |
|  | A green, floral, minty, lemonly aroma. |

This composition is added to an aqueous laundrying bath at a concentration of 0.20% (weight) at a temperature of 55° C., water hardness 7 grains/gallon and a pH of 10.0. Polyester and mixed polyester/cotton fabrics are laundered in the bath for a period of 10 minutes after which the fabrics are thoroughly rinsed with fresh water and dried at ambient temperatures. The fabrics are provided with a soil release finish. The head space above the fabrics has a pleasant faint aroma as indicated in Table II above.

What is claimed is:

1. A process for augmenting or enhancing the aroma of a fabric softener comprising the step of placing in intimate contact with a fabric softener base at least one cyclic chemical compound having the structure:

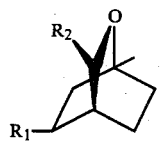

wherein $R_1$ is selected from the group consisting of hydrogen and methyl and $R_2$ is $C_3$–$C_5$ alkyl and alkenyl.

2. A fabric softener article comprising a non-woven cloth substrate and a substrate coating intimately admixed with a cyclic chemical compound having the structure:

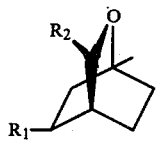

wherein $R_1$ is selected from the group consisting of hydrogen and methyl and $R_2$ is $C_3$–$C_5$ alkyl or alkenyl.

3. The process of claim 1 wherein the cyclic chemical compound has the structure:

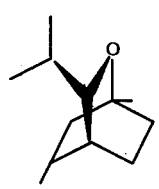

4. The process of claim 1 wherein the cyclic chemical compound has the structure:

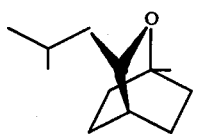

5. The process of claim 1 wherein the cyclic chemical compound has the structure:

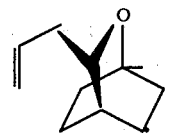

6. The process of claim 1 wherein the cyclic chemical compound has the structure:

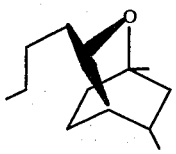

7. The process of claim 1 wherein the cyclic chemical compound has the structure:

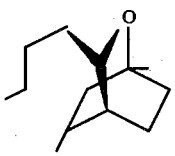

8. The process of claim 1 wherein the cyclic chemical compound has the structure:

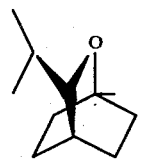

9. The process of claim 1 wherein the cyclic chemical compound has the structure:

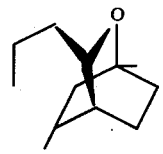

10. The process of claim 1 wherein the cyclic chemical compound has the structure:

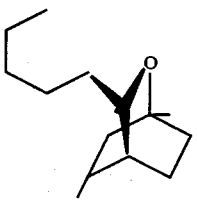

* * * * *